(12) United States Patent
Hendricksen et al.

(10) Patent No.: US 8,251,067 B2
(45) Date of Patent: Aug. 28, 2012

(54) BRONCHIAL FLOW CONTROL DEVICES WITH MEMBRANE SEAL

(75) Inventors: Michael Hendricksen, Redwood City, CA (US); Peter Wilson, Pacifica, CA (US); Ronald Hundertmark, San Mateo, CA (US); Antony J. Fields, San Francisco, CA (US)

(73) Assignee: Pulmonx Corporation, Redwood City, CA (US)

( * ) Notice: Subject to any disclaimer, the term of this patent is extended or adjusted under 35 U.S.C. 154(b) by 13 days.

(21) Appl. No.: 12/857,356

(22) Filed: Aug. 16, 2010

(65) Prior Publication Data
US 2011/0017207 A1    Jan. 27, 2011

Related U.S. Application Data

(63) Continuation of application No. 10/627,941, filed on Jul. 25, 2003, now Pat. No. 7,798,147, and a continuation-in-part of application No. 09/797,910, filed on Mar. 2, 2001, now Pat. No. 6,694,979, and a continuation-in-part of application No. 10/270,792, filed on Oct. 10, 2002, now Pat. No. 6,941,950.

(60) Provisional application No. 60/399,273, filed on Jul. 26, 2002, provisional application No. 60/429,902, filed on Nov. 27, 2002.

(51) Int. Cl.
| | |
|---|---|
| A61M 29/00 | (2006.01) |
| A61M 16/00 | (2006.01) |
| A61M 5/00 | (2006.01) |
| A61M 11/00 | (2006.01) |
| A61B 17/08 | (2006.01) |
| A61F 2/06 | (2006.01) |
| A61F 2/04 | (2006.01) |

(52) U.S. Cl. ......... 128/207.14; 128/200.26; 128/207.15; 128/207.16; 604/246; 604/247; 604/249; 604/256; 606/108; 606/191; 606/198; 606/200; 606/217; 623/1.24; 623/1.25; 623/1.26; 623/23.68; 623/23.7

(58) Field of Classification Search ............ 128/200.26, 128/207.14, 207.15, 207.16; 604/246, 247, 604/249, 256; 606/108, 191, 198, 200, 213, 606/217; 623/1.24, 1.25, 1.26, 23.68, 23.7
See application file for complete search history.

(56) References Cited

U.S. PATENT DOCUMENTS 2,981,254 A    4/1961   Vanderbilt
(Continued)

FOREIGN PATENT DOCUMENTS

EP    0 128 433 B1    4/1989
(Continued)

OTHER PUBLICATIONS

Al Jishi et al., "Selective Bronchial Occlusion for Treatment of Bullous Interstitial Emphysema and Bronchopleural Fistula." J. of Pediatric Surgery, 29:1545-1547, 1994.

(Continued)

*Primary Examiner* — Patricia Bianco
*Assistant Examiner* — Nihir Patel
(74) *Attorney, Agent, or Firm* — Wilson Sonsini Goodrich & Rosati

(57) ABSTRACT

Disclosed is a flow control device for a bronchial passageway. The device can includes a valve member that regulates fluid flow through the flow control device, a frame coupled to the valve member, and a membrane attached to the frame. At least a portion of the flow control device forms a seal with the interior wall of the bronchial passageway when the flow control device is implanted in the bronchial passageway. The membrane forms a fluid pathway from the seal into the valve member to direct fluid flowing through the bronchial passageway into the valve member.

12 Claims, 27 Drawing Sheets

U.S. PATENT DOCUMENTS

| | | |
|---|---|---|
| 3,657,744 A | 4/1972 | Ersek |
| 3,788,327 A | 1/1974 | Donowitz et al. |
| 3,874,388 A | 4/1975 | King et al. |
| 4,014,318 A | 3/1977 | Dockum et al. |
| 4,086,665 A | 5/1978 | Poirier |
| 4,212,463 A | 7/1980 | Repinski et al. |
| 4,250,873 A | 2/1981 | Bonnet |
| 4,302,854 A | 12/1981 | Runge |
| 4,477,930 A | 10/1984 | Totten et al. |
| 4,483,075 A | 11/1984 | Kundin |
| 4,566,465 A | 1/1986 | Arhan et al. |
| 4,586,491 A | 5/1986 | Carpenter |
| 4,710,192 A | 12/1987 | Liotta et al. |
| 4,732,152 A | 3/1988 | Wallsten et al. |
| 4,759,758 A | 7/1988 | Gabbay |
| 4,774,942 A | 10/1988 | Moellers |
| 4,795,449 A | 1/1989 | Schneider et al. |
| 4,808,183 A | 2/1989 | Panje |
| 4,819,664 A | 4/1989 | Nazari |
| 4,830,003 A | 5/1989 | Wolff et al. |
| 4,832,680 A | 5/1989 | Haber et al. |
| 4,846,836 A | 7/1989 | Reich |
| 4,850,999 A | 7/1989 | Planck |
| 4,852,568 A | 8/1989 | Kensey |
| 4,877,025 A | 10/1989 | Hanson |
| 4,879,998 A | 11/1989 | Moellers |
| 4,934,999 A | 6/1990 | Bader |
| 4,968,294 A | 11/1990 | Salama |
| 4,990,151 A | 2/1991 | Wallsten |
| 5,010,892 A | 4/1991 | Colvin et al. |
| 5,061,274 A | 10/1991 | Kensey |
| 5,116,360 A | 5/1992 | Pinchuk et al. |
| 5,116,564 A | 5/1992 | Jansen et al. |
| 5,123,919 A | 6/1992 | Sauter et al. |
| 5,151,105 A | 9/1992 | Kwan-Gett |
| 5,158,548 A | 10/1992 | Lau et al. |
| 5,161,524 A | 11/1992 | Evans |
| 5,271,385 A | 12/1993 | Bailey |
| 5,306,234 A | 4/1994 | Johnson |
| 5,352,240 A | 10/1994 | Ross |
| 5,358,518 A | 10/1994 | Camilli |
| 5,366,478 A | 11/1994 | Brinkerhoff et al. |
| 5,382,261 A | 1/1995 | Palmaz |
| 5,392,775 A | 2/1995 | Adkins et al. |
| 5,409,019 A | 4/1995 | Wilk |
| 5,411,507 A | 5/1995 | Heckele |
| 5,411,552 A | 5/1995 | Andersen et al. |
| 5,413,599 A | 5/1995 | Imachi et al. |
| 5,417,226 A | 5/1995 | Juma |
| 5,445,626 A | 8/1995 | Gigante |
| 5,453,090 A | 9/1995 | Martinez et al. |
| 5,486,154 A | 1/1996 | Kelleher |
| 5,499,995 A | 3/1996 | Teirstein |
| 5,500,014 A | 3/1996 | Quijano et al. |
| 5,562,608 A | 10/1996 | Sekins et al. |
| 5,588,424 A | 12/1996 | Insler et al. |
| 5,645,519 A | 7/1997 | Lee et al. |
| 5,645,565 A | 7/1997 | Rudd et al. |
| 5,649,906 A | 7/1997 | Gory et al. |
| 5,660,175 A | 8/1997 | Dayal |
| 5,662,713 A | 9/1997 | Andersen et al. |
| 5,683,451 A | 11/1997 | Lenker et al. |
| 5,697,968 A | 12/1997 | Rogers et al. |
| 5,755,770 A | 5/1998 | Ravenscroft |
| 5,800,339 A | 9/1998 | Salama |
| 5,803,080 A | 9/1998 | Freitag |
| 5,840,081 A | 11/1998 | Andersen et al. |
| 5,851,232 A | 12/1998 | Lois |
| 5,855,587 A | 1/1999 | Hyon et al. |
| 5,855,597 A | 1/1999 | Jayaraman |
| 5,855,601 A | 1/1999 | Bessler et al. |
| 5,910,144 A | 6/1999 | Hayashi |
| 5,944,738 A | 8/1999 | Amplatz et al. |
| 5,947,997 A | 9/1999 | Pavcnik et al. |
| 5,954,766 A | 9/1999 | Zadno-Azizi et al. |
| 5,957,949 A | 9/1999 | Leonhardt et al. |
| 5,976,174 A | 11/1999 | Ruiz |
| 5,980,455 A | 11/1999 | Daniel et al. |
| 5,984,965 A | 11/1999 | Knapp et al. |
| 6,007,575 A | 12/1999 | Samuels |
| 6,009,614 A | 1/2000 | Morales |
| 6,020,380 A | 2/2000 | Killian |
| 6,022,312 A | 2/2000 | Chaussy et al. |
| 6,027,508 A | 2/2000 | Ren et al. |
| 6,027,525 A | 2/2000 | Suh et al. |
| 6,033,359 A | 3/2000 | Doi |
| 6,039,333 A | 3/2000 | Hamblin |
| 6,042,554 A | 3/2000 | Rosenman et al. |
| 6,051,022 A | 4/2000 | Cai et al. |
| 6,068,635 A | 5/2000 | Gianotti |
| 6,068,638 A | 5/2000 | Makower |
| 6,077,291 A | 6/2000 | Das |
| 6,083,255 A | 7/2000 | Laufer et al. |
| 6,110,201 A | 8/2000 | Quijano et al. |
| 6,123,663 A | 9/2000 | Rebuffat |
| 6,135,729 A | 10/2000 | Aber |
| 6,135,991 A | 10/2000 | Muni et al. |
| 6,141,855 A | 11/2000 | Morales |
| 6,143,021 A | 11/2000 | Staehle |
| 6,162,245 A | 12/2000 | Jayaraman |
| 6,168,614 B1 | 1/2001 | Andersen et al. |
| 6,174,323 B1 | 1/2001 | Biggs et al. |
| 6,183,520 B1 | 2/2001 | Pintauro et al. |
| 6,190,381 B1 | 2/2001 | Olsen et al. |
| 6,193,748 B1 | 2/2001 | Thompson et al. |
| 6,200,333 B1 | 3/2001 | Laufer |
| 6,206,918 B1 | 3/2001 | Campbell et al. |
| 6,234,996 B1 | 5/2001 | Bagaoisan et al. |
| 6,240,615 B1 | 6/2001 | Kimes et al. |
| 6,245,102 B1 | 6/2001 | Jayaraman |
| 6,247,471 B1 | 6/2001 | Bower et al. |
| 6,258,100 B1 | 7/2001 | Alferness et al. |
| 6,270,527 B1 | 8/2001 | Campbell et al. |
| 6,280,464 B1 | 8/2001 | Hayashi |
| 6,287,290 B1 | 9/2001 | Perkins et al. |
| 6,293,951 B1 * | 9/2001 | Alferness et al. ............. 606/108 |
| 6,302,893 B1 | 10/2001 | Limon et al. |
| D450,607 S | 11/2001 | Tomiser et al. |
| 6,312,407 B1 | 11/2001 | Zadno-Azizi et al. |
| 6,325,777 B1 | 12/2001 | Zadno-Azizi et al. |
| 6,325,778 B1 | 12/2001 | Zadno-Azizi et al. |
| 6,327,772 B1 | 12/2001 | Zadno-Azizi et al. |
| 6,328,689 B1 | 12/2001 | Gonzalez |
| 6,350,278 B1 | 2/2002 | Lenker et al. |
| 6,355,014 B1 | 3/2002 | Zadno-Azizi et al. |
| 6,391,051 B2 | 5/2002 | Sullivan, III et al. |
| 6,398,775 B1 | 6/2002 | Perkins et al. |
| 6,402,754 B1 | 6/2002 | Gonzalez |
| 6,416,554 B1 | 7/2002 | Alferness et al. |
| 6,450,976 B2 | 9/2002 | Korotko et al. |
| 6,458,076 B1 | 10/2002 | Pruitt |
| 6,485,407 B2 | 11/2002 | Alferness et al. |
| 6,491,706 B1 | 12/2002 | Alferness et al. |
| 6,493,589 B1 | 12/2002 | Medhkour et al. |
| 6,510,846 B1 | 1/2003 | O'Rourke |
| 6,524,259 B2 | 2/2003 | Baxter-Jones et al. |
| 6,527,761 B1 | 3/2003 | Soltesz et al. |
| 6,558,318 B1 | 5/2003 | Daniel et al. |
| 6,592,594 B2 | 7/2003 | Rimbaugh et al. |
| 6,632,243 B1 | 10/2003 | Zadno-Azizi et al. |
| 6,679,264 B1 | 1/2004 | Deem et al. |
| 6,685,739 B2 | 2/2004 | DiMatteo et al. |
| 6,694,979 B2 | 2/2004 | Deem et al. |
| 6,699,231 B1 | 3/2004 | Sterman et al. |
| 6,802,846 B2 | 10/2004 | Hauschild et al. |
| 6,833,530 B2 | 12/2004 | Kim |
| 6,840,243 B2 | 1/2005 | Deem et al. |
| 6,878,141 B1 | 4/2005 | Perkins et al. |
| 6,896,690 B1 | 5/2005 | Lambrecht et al. |
| 6,901,927 B2 | 6/2005 | Deem et al. |
| 6,904,909 B2 | 6/2005 | Andreas et al. |
| 6,941,950 B2 | 9/2005 | Wilson et al. |
| 7,036,509 B2 | 5/2006 | Rapacki et al. |
| 7,412,977 B2 | 8/2008 | Fields et al. |
| 7,422,584 B2 | 9/2008 | Loomas et al. |
| 7,717,115 B2 | 5/2010 | Barrett et al. |
| 7,798,147 B2 | 9/2010 | Hendricksen et al. |

| | | | |
|---|---|---|---|
| 7,814,912 B2 | 10/2010 | George et al. | |
| 7,854,228 B2 | 12/2010 | Wilson et al. | |
| 2001/0025132 A1 | 9/2001 | Alferness et al. | |
| 2001/0027323 A1 | 10/2001 | Sullivan, III et al. | |
| 2001/0037808 A1 | 11/2001 | Deem et al. | |
| 2001/0041906 A1 | 11/2001 | Gonzalez | |
| 2001/0051799 A1 | 12/2001 | Ingenito | |
| 2001/0052344 A1 | 12/2001 | Doshi | |
| 2001/0056274 A1 | 12/2001 | Perkins et al. | |
| 2002/0007831 A1 | 1/2002 | Davenport et al. | |
| 2002/0026233 A1 | 2/2002 | Shaknovich | |
| 2002/0062120 A1 | 5/2002 | Perkins et al. | |
| 2002/0077593 A1 | 6/2002 | Perkins et al. | |
| 2002/0077696 A1 | 6/2002 | Zadno-Azizi et al. | |
| 2002/0087153 A1 | 7/2002 | Roschak et al. | |
| 2002/0095209 A1 | 7/2002 | Zadno-Azizi et al. | |
| 2002/0111619 A1 | 8/2002 | Keast et al. | |
| 2002/0111620 A1 | 8/2002 | Cooper et al. | |
| 2002/0112729 A1 | 8/2002 | DeVore et al. | |
| 2002/0138135 A1 | 9/2002 | Duerig et al. | |
| 2003/0018327 A1 | 1/2003 | Truckai et al. | |
| 2003/0018344 A1 | 1/2003 | Kaji et al. | |
| 2003/0050648 A1 | 3/2003 | Alferness et al. | |
| 2003/0070682 A1 | 4/2003 | Wilson et al. | |
| 2003/0070683 A1 | 4/2003 | Deem et al. | |
| 2003/0075169 A1 | 4/2003 | Deem et al. | |
| 2003/0075170 A1 | 4/2003 | Deem et al. | |
| 2003/0083671 A1* | 5/2003 | Rimbaugh et al. | 606/108 |
| 2003/0127090 A1 | 7/2003 | Gifford et al. | |
| 2003/0164168 A1 | 9/2003 | Shaw et al | |
| 2003/0181922 A1 | 9/2003 | Alferness | |
| 2003/0183235 A1 | 10/2003 | Rimbaugh et al. | |
| 2003/0192550 A1 | 10/2003 | Deem et al. | |
| 2003/0192551 A1 | 10/2003 | Deem et al. | |
| 2003/0199972 A1 | 10/2003 | Zadno-Azizi et al. | |
| 2003/0212452 A1 | 11/2003 | Zadno-Azizi et al. | |
| 2003/0228344 A1 | 12/2003 | Fields et al. | |
| 2004/0016435 A1 | 1/2004 | Deem et al. | |
| 2004/0039250 A1 | 2/2004 | Tholfsen et al. | |
| 2004/0060563 A1 | 4/2004 | Rapacki et al. | |
| 2004/0074491 A1 | 4/2004 | Hendricksen et al. | |
| 2004/0089306 A1 | 5/2004 | Hundertmark et al. | |
| 2004/0134487 A1 | 7/2004 | Deem et al. | |
| 2004/0154621 A1 | 8/2004 | Deem et al. | |
| 2004/0211434 A1 | 10/2004 | Loomas et al. | |
| 2005/0016530 A1 | 1/2005 | McCutcheon et al. | |
| 2005/0051163 A1 | 3/2005 | Deem et al. | |
| 2005/0066974 A1 | 3/2005 | Fields et al. | |
| 2005/0087137 A1 | 4/2005 | Park et al. | |
| 2005/0145253 A1 | 7/2005 | Wilson et al. | |
| 2005/0161048 A1 | 7/2005 | Rapacki et al. | |
| 2005/0166925 A1 | 8/2005 | Wilson et al. | |
| 2005/0178389 A1 | 8/2005 | Shaw et al. | |
| 2005/0196344 A1 | 9/2005 | McCutcheon et al. | |
| 2006/0020347 A1 | 1/2006 | Barrett et al. | |
| 2011/0092767 A1 | 4/2011 | George et al. | |

FOREIGN PATENT DOCUMENTS

| | | | |
|---|---|---|---|
| EP | 0346564 A1 | 12/1989 | |
| EP | 0621015 A1 | 10/1994 | |
| EP | 0 621 015 B1 | 3/1998 | |
| EP | 1 078 601 A2 | 2/2001 | |
| EP | 1 151 729 A1 | 11/2001 | |
| GB | 2324729 A | 4/1998 | |
| GB | 2373445 A | 9/2002 | |
| JP | 2000-292108 A | 10/2000 | |
| RU | 2140211 C1 | 10/1999 | |
| SU | 852321 A1 | 7/1981 | |
| SU | 1371700 A1 | 2/1988 | |
| SU | 1593651 A1 | 9/1990 | |
| WO | WO 94/26175 A1 | 11/1994 | |
| WO | WO 95/32018 A1 | 11/1995 | |
| WO | WO 96/34582 A1 | 11/1996 | |
| WO | WO 97/44085 A2 | 11/1997 | |
| WO | WO 98/00840 A1 | 1/1998 | |
| WO | WO 98/19633 A1 | 5/1998 | |
| WO | WO 98/39047 A1 | 9/1998 | |
| WO | WO 98/44854 A1 | 10/1998 | |
| WO | WO 98/48706 A1 | 11/1998 | |
| WO | WO 99/01076 A1 | 1/1999 | |
| WO | WO 99/13801 A1 | 3/1999 | |
| WO | WO 99/26692 A1 | 6/1999 | |
| WO | WO 99/32040 A1 | 7/1999 | |
| WO | WO 99/42059 A2 | 8/1999 | |
| WO | WO 99/42161 A2 | 8/1999 | |
| WO | WO 99/64109 A1 | 12/1999 | |
| WO | WO 00/15149 A1 | 3/2000 | |
| WO | WO 00/18330 A1 | 4/2000 | |
| WO | WO 00/42950 A2 | 7/2000 | |
| WO | WO 00/51510 A1 | 9/2000 | |
| WO | WO 00/62699 A2 | 10/2000 | |
| WO | WO 00/78386 A1 | 12/2000 | |
| WO | WO 00/78407 A1 | 12/2000 | |
| WO | WO 01/02042 A1 | 1/2001 | |
| WO | WO 01/03642 A1 | 1/2001 | |
| WO | WO 01/05334 A1 | 1/2001 | |
| WO | WO 01/10313 A1 | 2/2001 | |
| WO | WO 01/10314 A2 | 2/2001 | |
| WO | WO 01/12104 A1 | 2/2001 | |
| WO | WO 01/13839 A1 | 3/2001 | |
| WO | WO 01/13908 A2 | 3/2001 | |
| WO | WO 01/28433 A1 | 4/2001 | |
| WO | WO 01/45590 A2 | 6/2001 | |
| WO | WO 01/49213 A2 | 7/2001 | |
| WO | WO 01/54585 A1 | 8/2001 | |
| WO | WO 01/54625 A1 | 8/2001 | |
| WO | WO 01/54685 A1 | 8/2001 | |
| WO | WO 01/66190 A2 | 9/2001 | |
| WO | WO 01/74271 A1 | 10/2001 | |
| WO | WO 01/87170 A1 | 10/2001 | |
| WO | WO 01/89366 A2 | 11/2001 | |
| WO | WO 01/95786 A2 | 12/2001 | |
| WO | WO 02/05884 A2 | 1/2002 | |
| WO | WO 02/22072 A2 | 3/2002 | |
| WO | WO 02/32333 A1 | 4/2002 | |
| WO | WO 02/34322 A2 | 5/2002 | |
| WO | WO 02/38038 A2 | 5/2002 | |
| WO | WO 02/47575 A2 | 6/2002 | |
| WO | WO 02/056794 A2 | 7/2002 | |
| WO | WO 02/064045 A1 | 8/2002 | |
| WO | WO 02/064190 A2 | 8/2002 | |
| WO | WO 02/069823 A2 | 9/2002 | |
| WO | WO 02/094087 A1 | 11/2002 | |
| WO | WO 03/020338 A2 | 3/2003 | |
| WO | WO 03/022124 A2 | 3/2003 | |
| WO | WO 03/030975 A2 | 4/2003 | |
| WO | WO 03/079944 A1 | 10/2003 | |
| WO | WO 03/088912 A1 | 10/2003 | |
| WO | WO 03/020338 A3 | 11/2003 | |
| WO | WO 03/099164 A1 | 12/2003 | |
| WO | WO 2004/010845 A2 | 2/2004 | |
| WO | WO 2004/049974 A2 | 6/2004 | |
| WO | WO 2004/049974 A3 | 8/2004 | |

OTHER PUBLICATIONS

Autocath.RTM. 100—Nonsurgical, Intraurethral Bladder Control Device for Incontinent and Retentive Women—Dr. Kulisz's Development.

Derwent Abstract WPI Acc No. 2001-019895/200103.

Derwent citing Russian Patent No. RU 2140211, published Oct. 27, 1999, for: "Method of surgical treatment of patients with pathology of respiratory organs complicated with pulmonary hemorrhages".

Derwent citing Soviet Union Patent No. SU 852-321, published Jul. 8, 1981, for: "Treatment for acute pulmonary and pleural disease in children—by pneumo-abcessotomy simultaneous with occlusion of affected lung part".

Derwent# 007607249 WPI Acc. No. 1988-241181/198834 (citing Russian Application No. SU4026409, published Feb. 21, 1986), Russian Patent No. SU 1371700.

Derwent# 008650867 WPI Acc. No. 1991-154896/199121 (citing Russian Application No. SU4280143, published Jul. 7, 1987), Russian Patent No. SU 1593651.

Harris et al., "The Experimental Production in Dogs of Emphysema with Associated Asthmatic Syndrome by Means of an Intratracheal Ball Valve", J. Lab. Clini. Med., 9(iv):75-88, 1919.

Lewis et al., "Pulmonary Interstitial Emphysema: Selective Broncial Occlusion with a Swan-Ganz Catheter", Archives of Disease in Childhood, 63:313-315, 1988.

Mathew et al., "Selective bronchial obstruction for treatment of bullous interstitial emphysema." J. of Ped., 96:475-477, 1980.

Okada et al., "Emergent Bronchofiberoptic Bronchial Occlusion for Intractable Pneumothorax with Severe Emphysema", The Jap. J. of Thor. and Cardio. Sur., 46:1078-1081, 1998.

Puhakka et al., "Acute Bronchial Obstruction: An Experimental Rabbit Model Study", Int. J. of Pediatric Otorhinolaryngology, 18:107-118, 1989.

Snider et al., The Definition of Emphysema: Report of the National Heart Lung and Blood Institute, Division of Lung Diseases Workshop, Am. Rev. Respir. Dis., 132:182-185, 1985.

Woodring et al., "Pneumothorax ex Vacuo", Chest, 100:1102-1105, 1996.

International search report dated Jul. 9, 2004 for PCT/US2003/037890.

International search report dated Dec. 10, 2003 for PCT/US2003/023295.

* cited by examiner

BRONCHIAL FLOW CONTROL DEVICES WITH MEMBRANE SEAL

CROSS-REFERENCES TO RELATED APPLICATIONS

This application is a continuation of U.S. patent application Ser. No. 10/627,941, filed Jul. 25, 2003, now U.S. Pat. No. 7,798,147, which claimed priority of co-pending U.S. Provisional Patent Application Ser. No. 60/399,273 entitled "Implantable Bronchial Isolation Devices", filed Jul. 26, 2002 and copending U.S. Provisional Patent Application Ser. No. 60/429,902 entitled "Implantable Bronchial Isolation Devices", filed Nov. 27, 2002, and was a continuation-in-part of the following patent applications: (1) U.S. patent application Ser. No. 09/797,910, now U.S. Ser. No. 6,694,979, entitled "Methods and Devices for Use in Performing Pulmonary Procedures", filed Mar. 2, 2001; and (2) U.S. patent application Ser. No. 10/270,792, now U.S. Pat. No. 6,941,950, entitled "Bronchial Flow Control Devices and Methods of Use", filed Oct. 10, 2002. Priority of the aforementioned filing dates are hereby claimed, and the disclosures of the Non-provisional and Provisional Patent Applications are hereby incorporated by reference in their entirety.

BACKGROUND OF THE INVENTION

1. Field of the Invention

This invention relates generally to methods and devices for use in performing pulmonary procedures and, more particularly, to devices and procedures for treating lung diseases.

2. Description of the Related Art

Pulmonary diseases, such as chronic obstructive pulmonary disease, (COPO), reduce the ability of one or both lungs to fully expel air during the exhalation phase of the breathing cycle. The term "Chronic Obstructive Pulmonary Disease" (COPD) refers to a group of diseases that share a major symptom, dyspnea. Such diseases are accompanied by chronic or recurrent obstruction to air flow within the lung. Because of the increase in environmental pollutants, cigarette smoking, and other noxious exposures, the incidence of COPO has increased dramatically in the last few decades and now ranks as a major cause of activity-restricting or bed-confining disability in the United States. COPO can include such disorders as chronic bronchitis, bronchiectasis, asthma, and emphysema. While each has distinct anatomic and clinical considerations, many patients may have overlapping characteristics of damage at both the acinar (as seen in emphysema) and the bronchial (as seen in bronchitis) levels.

Emphysema is a condition of the lung characterized by the abnormal permanent enlargement of the airspaces distal to the terminal bronchiole, accompanied by the destruction of their walls, and without obvious fibrosis. It is known that emphysema and other pulmonary diseases reduce the ability of one or both lungs to fully expel air during the exhalation phase of the breathing cycle. One of the effects of such diseases is that the diseased lung tissue is less elastic than healthy lung tissue, which is one factor that prevents full exhalation of air. During breathing, the diseased portion of the lung does not fully recoil due to the diseased (e.g., emphysematic) lung tissue being less elastic than healthy tissue. Consequently, the diseased lung tissue exerts a relatively low driving force, which results in the diseased lung expelling less air volume than a healthy lung.

The problem is further compounded by the diseased, less elastic tissue that surrounds the very narrow airways that lead to the alveoli, which are the air sacs where oxygen-carbon dioxide exchange occurs. The diseased tissue has less tone than healthy tissue and is typically unable to maintain the narrow airways open until the end of the exhalation cycle. This traps air in the lungs and exacerbates the already-inefficient breathing cycle. The trapped air causes the tissue to become hyper-expanded and no longer able to effect efficient oxygen-carbon dioxide exchange.

In addition, hyper-expanded, diseased lung tissue occupies more of the pleural space than healthy lung tissue. In most cases, a portion of the lung is diseased while the remaining part is relatively healthy and, therefore, still able to somewhat efficiently carry out oxygen exchange. By taking up more of the pleural space, the hyper-expanded lung tissue reduces the amount of space available to accommodate the healthy, functioning lung tissue. As a result, the hyper-expanded lung tissue causes inefficient breathing due to its own reduced functionality and because it adversely affects the functionality of adjacent relatively healthier tissue.

Lung reduction surgery is a conventional method of treating emphysema. According to the lung reduction procedure, a diseased portion of the lung is surgically removed, which makes more of the pleural space available to accommodate the functioning, healthy portions of the lung. The lung is typically accessed through a median sternotomy or small lateral thoracotomy. A portion of the lung, typically the periphery of the upper lobe, is freed from the chest wall and then resected, e.g., by a stapler lined with bovine pericardium to reinforce the lung tissue adjacent the cut line and also to prevent air or blood leakage. The chest is then closed and tubes are inserted to remove air and fluid from the pleural cavity. The conventional surgical approach is relatively traumatic and invasive, and, like most surgical procedures, is not a viable option for all patients.

Some recently proposed treatments include the use of devices that isolate a diseased region of the lung in order to reduce the volume of the diseased region, such as by collapsing the diseased lung region. According to such treatments, isolation devices are implanted in airways feeding the targeted region of the lung to regulate fluid flow to the diseased lung region in order to fluidly isolate the region of the lung. These implanted isolation devices can be, for example, one-way valves that allow flow in the exhalation direction only, occluders or plugs that prevent flow in either direction, or two-way valves that control flow in both directions. However, such devices are still in the development stages. Thus, there is much need for improvement in the design and functionality of such isolation devices.

In view of the foregoing, there is a need for improved methods and devices for regulating fluid flow to a diseased lung region.

BRIEF SUMMARY OF THE INVENTION

Disclosed are methods and devices for regulating fluid flow to and from a region of a patient's lung, such as to achieve a desired fluid flow dynamic to a lung region during respiration and/or to induce collapse in one or more lung regions. In one aspect of the invention, there is disclosed a flow control device for a bronchial passageway. The flow control device comprises a valve member that regulates fluid flow through the flow control device, the valve having a default shape. The device further comprises a frame coupled to the valve member, the frame including a valve protector region that at least partially surrounds the valve member to maintain the default shape; and a retainer region connected to the valve protector region, the retainer region being formed of a plurality of interconnected struts configured to engage an interior wall of the bronchial passageway to retain the flow control device in a fixed location therein. The retainer region is movable from a contracted state suitable for introduction into the bronchial passageway to an expanded state suitable for engaging the interior wall of the bronchial passageway. The device further comprises a membrane covering at least a portion of the retainer region, wherein at least a portion of the flow control device forms a seal with the interior wall of the bronchial passageway when the flow control device is implanted in the bronchial passageway, and wherein the membrane provides a fluid pathway from the seal to the valve member to direct fluid flowing through the bronchial passageway into the valve member.

Also disclosed is a flow control device for a bronchial passageway. The device comprises a valve member that regulates fluid flow through the flow control device and has a default shape. The device further comprises a frame formed of a plurality of interconnected struts configured to engage an interior wall of the bronchial passageway to retain the flow control device in a fixed location therein. The frame is movable from a contracted state suitable for introduction into the bronchial passageway to an expanded state suitable for engaging the interior wall of the bronchial passageway. The device further comprises a valve protector at least partially surrounding the valve member configured to maintain the valve member in the default shape, the valve protector being collapsible from the default shape to a collapsed shape. The device further comprises a membrane covering at least a portion of the frame, wherein at least a portion of the flow control device forms a seal with the interior wall of the bronchial passageway when the flow control device is implanted in the bronchial passageway, and wherein the membrane provides a fluid pathway from the seal to the valve member to direct fluid flowing through the bronchial passageway into the valve member.

Also disclosed is a flow control device for a bronchial passageway. The device comprises a valve member that regulates fluid flow through the flow control device; a frame formed of a plurality of interconnected struts configured to engage an interior wall of the bronchial passageway to retain the flow control device in a fixed location therein, the frame being movable from a contracted state suitable for introduction into the bronchial passageway to an expanded state suitable for engaging the interior wall of the bronchial passageway; and at least one retention prong extending from the frame and configured to engage the interior wall of the bronchial passageway to resist migration therein.

Also disclosed is a flow control device for a bronchial passageway, the flow control device comprises a valve member that regulates fluid flow through the flow control device; a frame configured to engage an interior wall of the bronchial passageway to retain the flow control device in a fixed location therein, the frame being movable from a contracted state suitable for introduction into the bronchial passageway to an expanded state suitable for engaging the interior wall of the bronchial passageway; and a membrane covering at least a portion of the frame, wherein at least a portion of the flow control device forms a seal with the interior wall of the bronchial passageway when the flow control device is implanted in the bronchial passageway, and wherein the membrane provides a fluid pathway from the seal to the valve member to direct fluid flowing through the bronchial passageway into the valve member.

Also disclosed is a flow control device for a bronchial passageway. The device comprises a valve member that regulates fluid flow through the flow control device; a frame coupled to the valve member; and a membrane attached to the frame, wherein at least a portion of the flow control device forms a seal with the interior wall of the bronchial passageway when the flow control device is implanted in the bronchial passageway, and wherein the membrane forms a fluid pathway from the seal into the valve member to direct fluid flowing through the bronchial passageway into the valve member.

Other features and advantages of the present invention should be apparent from the following description of various embodiments, which illustrate, by way of example, the principles of the invention.

DETAILED DESCRIPTION OF THE INVENTION

Unless defined otherwise, all technical and scientific terms used herein have the same meaning as is commonly understood by one of skill in the art to which the invention(s) belong. Disclosed are various devices and method for treating bronchopulmonary diseases.

Disclosed are various embodiments of bronchial isolation devices 610 that can be used to isolate a diseased region of the lung in order to modify the air flow to the lung region or to achieve volume reduction or collapse of the lung region. One or more of the bronchial isolation devices 610 are implanted in bronchial passageways that feed fluid to a targeted region of the lung. The bronchial isolation devices 610 block or regulate fluid flow to the diseased lung region through one or more bronchial passageways that feed air to the targeted lung region.

Figure 1:
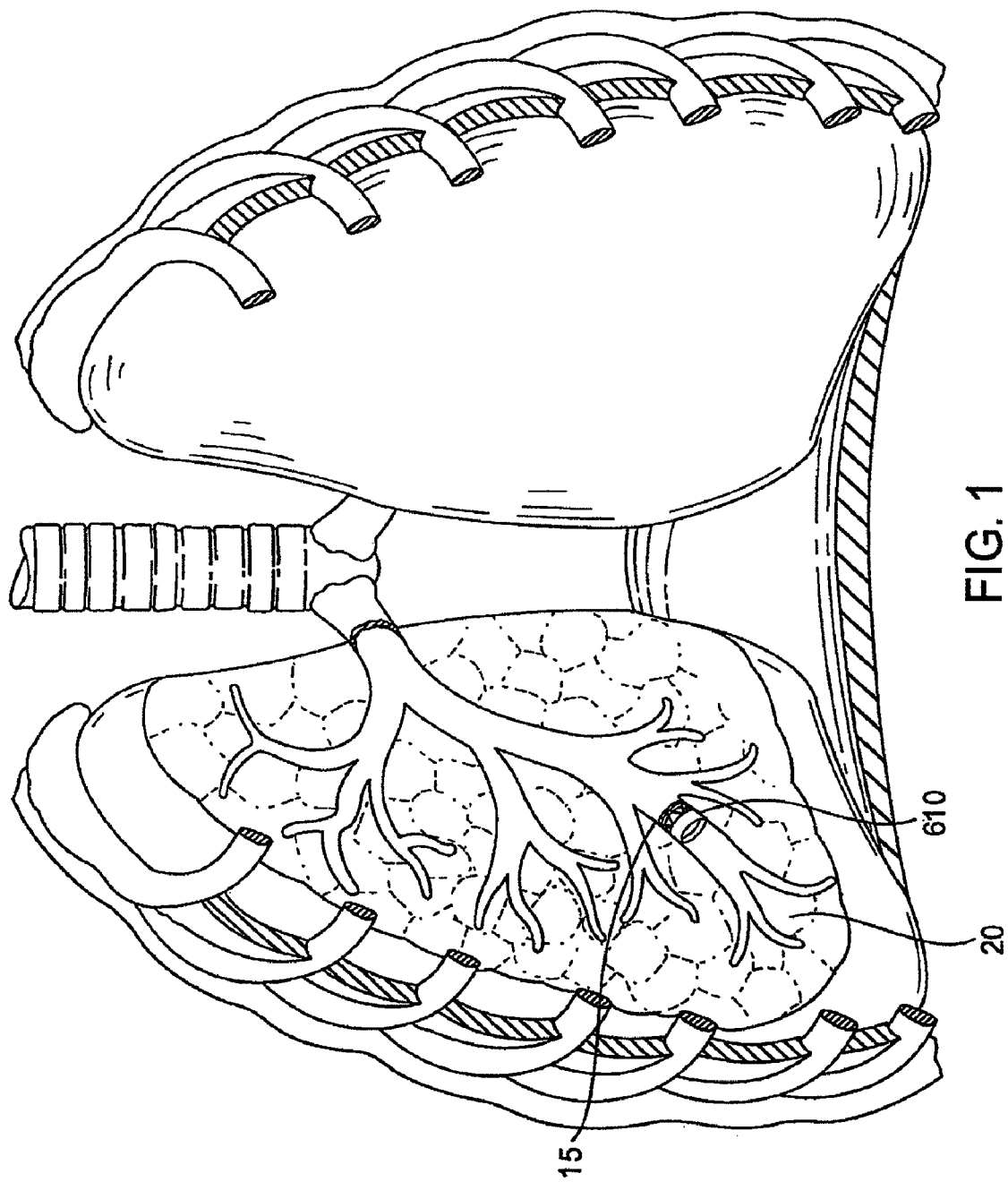
FIG. 1 shows an anterior view of a pair of human lungs and a bronchial tree with a bronchial isolation device implanted in a bronchial passageway to bronchially isolate a region of the lung.

As shown in FIG. 1, the bronchial isolation of the targeted lung region is accomplished by implanting a bronchial isolation device 610 into a bronchial passageway 15 that feeds air to a targeted lung region 20. The bronchial isolation device 610 regulates airflow through the bronchial passageway 15 in which the bronchial isolation device 10 is implanted. Various embodiments of bronchial isolation devices are described herein.

Exemplary Lung Regions. Throughout this disclosure, reference is made to the term "lung region". As used herein, the term "lung region" refers to a defined division or portion of a lung. For purposes of example, lung regions are described herein with reference to human lungs, wherein some exemplary lung regions include lung lobes and lung segments. Thus, the term "lung region" as used herein can refer. For example, to a lung lobe or a lung segment. Such nomenclature conforms to nomenclature for portions of the lungs that are known to those skilled in the art. However, it should be appreciated that the term "lung region" does not necessarily refer to a lung lobe or a lung segment, but can refer to some other defined division or portion of a human or non-human lung.

Figure 2:
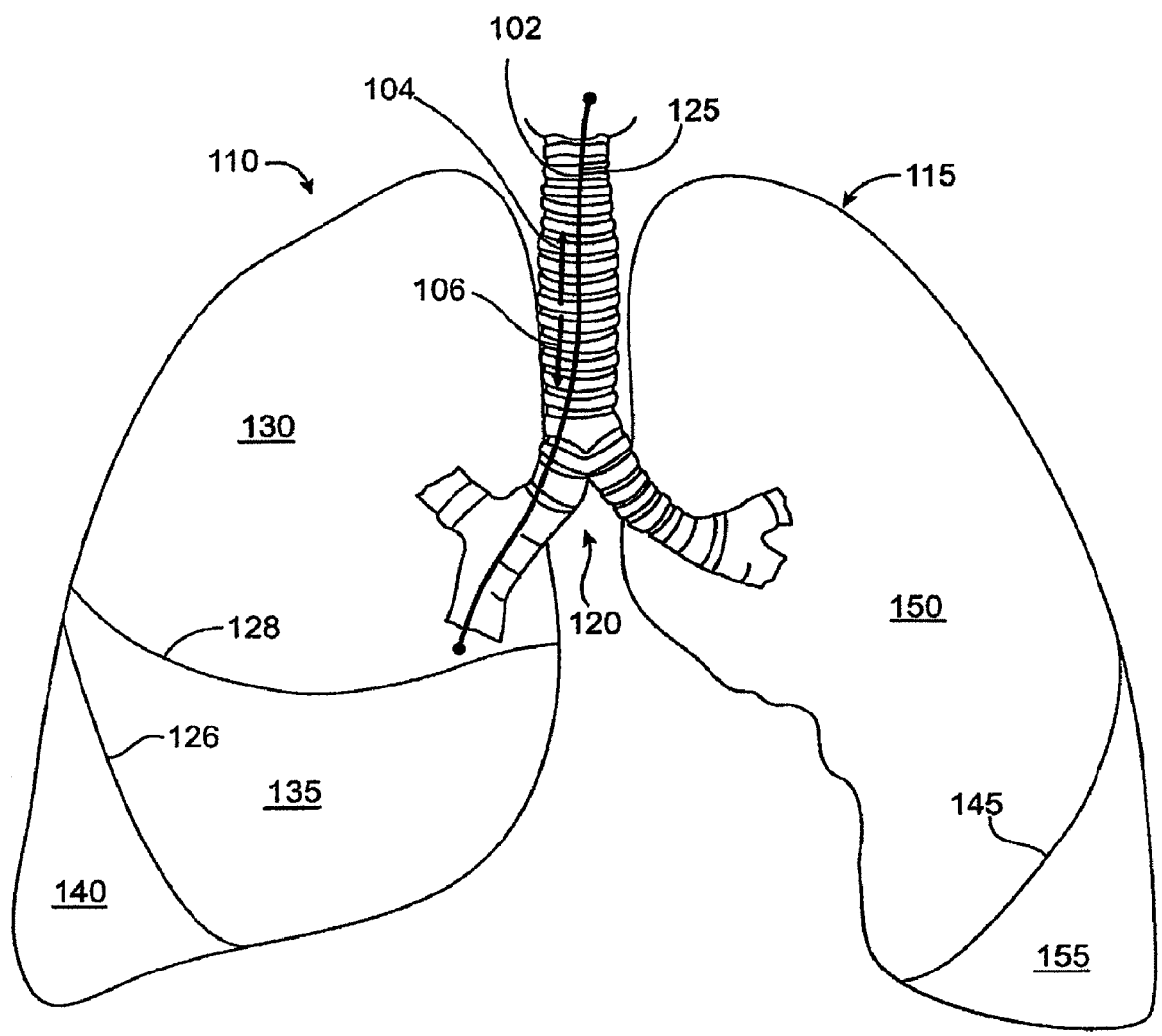
FIG. 2 shows an anterior view of a pair of human lungs and a bronchial tree.

FIG. 2 shows an anterior view of a pair of human lungs 110, 115 and a bronchial tree 120 that provides a fluid pathway into and out of the lungs 110, 115 from a trachea 125, as will be known to those skilled in the art. As used herein, the term "fluid" can refer to a gas, a liquid, or a combination of gas(es) and liquid(s). For clarity of illustration, FIG. 2 shows only a portion of the bronchial tree 120, which is described in more detail below with reference to FIG. 5.

Throughout this description, certain terms are used that refer to relative directions or locations along a path defined from an entryway into the patient's body (e.g., the mouth or nose) to the patient's lungs. The path of airflow into the lungs generally begins at the patient's mouth or nose, travels through the trachea into one or more bronchial passageways, and terminates at some point in the patient's lungs. For example, FIG. 2 shows a path 102 that travels through the trachea 125 and through a bronchial passageway into a location in the right lung 110. The term "proximal direction" refers to the direction along such a path 102 that points toward the patient's mouth or nose and away from the patient's lungs. In other words, the proximal direction is generally the same as the expiration direction when the patient breathes. The arrow 104 in FIG. 2 points in the proximal or expiratory direction. The term "distal direction" refers to the direction along such a path 102 that points toward the patient's lung and away from the mouth or nose. The distal direction is generally the same as the inhalation or inspiratory direction when the patient breathes. The arrow 106 in FIG. 2 points in the distal or inhalation direction.

The lungs include a right lung 110 and a left lung 115. The right lung 110 includes lung regions comprised of three lobes, including a right upper lobe 130, a right middle lobe 135, and a right lower lobe 140. The lobes 130, 135, 140 are separated by two interlobar fissures, including a right oblique fissure 126 and a right transverse fissure 128. The right oblique fissure 126 separates the right lower lobe 140 from the right upper lobe 130 and from the right middle lobe 135. The right transverse fissure 128 separates the right upper lobe 130 from the right 10 middle lobe 135.

As shown in FIG. 2, the left lung 115 includes lung regions comprised of two lobes, including the left upper lobe 150 and the left lower lobe 155. An interlobar fissure comprised of a left oblique fissure 145 of the left lung 115 separates the left upper lobe 150 from the left lower lobe 155. The lobes 130, 15 135, 140, 150, 155 are directly supplied air via respective lobar bronchi, as described in detail below.

Figure 3:
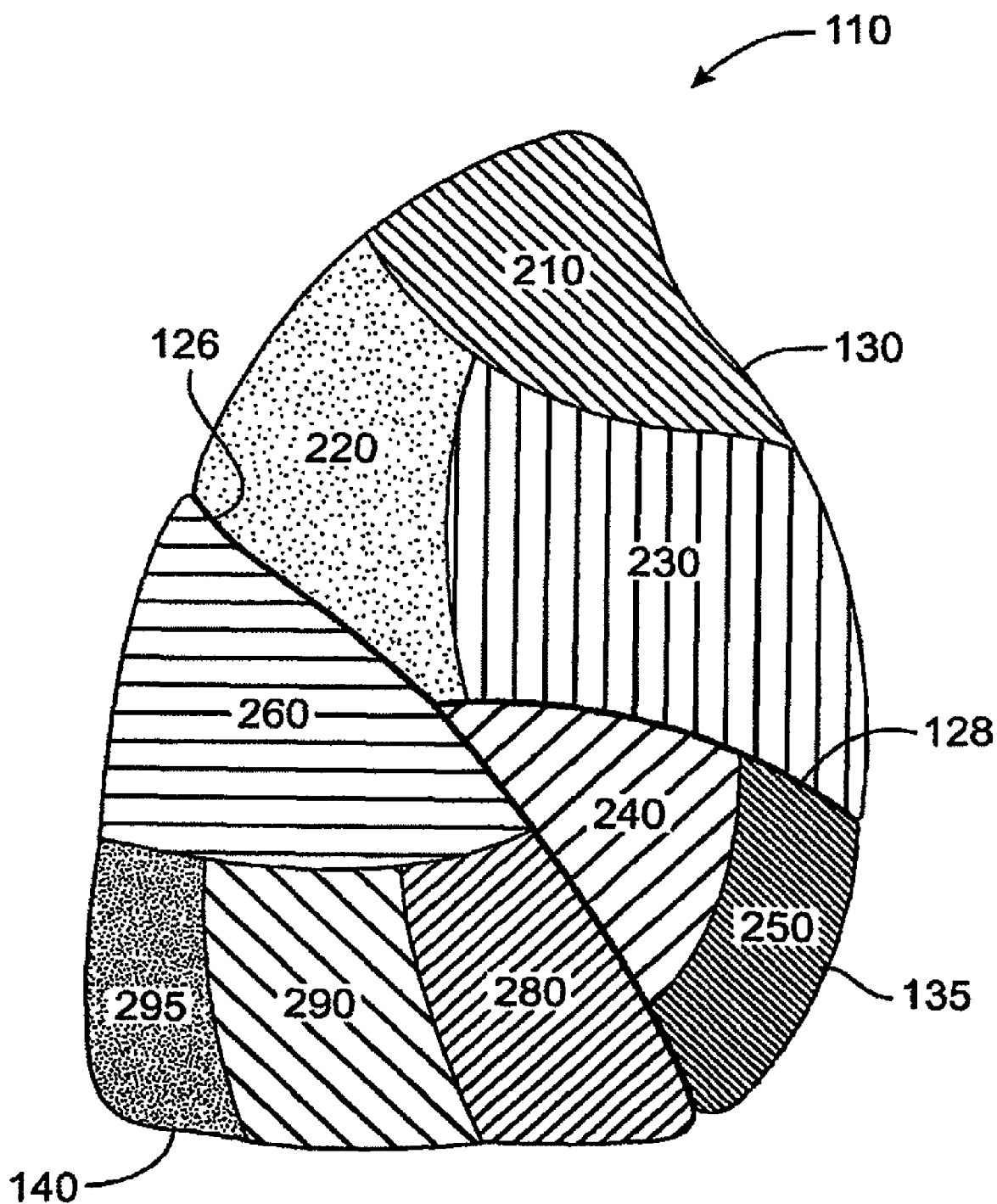
FIG. 3 shows a lateral view of the right lung.

FIG. 3 is a lateral view of the right lung 110. The right lung 110 is subdivided into lung regions comprised of a plurality of bronchopulmonary segments. Each bronchopulmonary segment is directly supplied air by a corresponding segmental tertiary bronchus, as described below. The bronchopulmonary segments of the right lung 110 include a right apical segment 210, a right posterior segment 220, and a right anterior segment 230, all of which are disposed in the right upper lobe 130. The right lung bronchopulmonary segments further include a right lateral segment 240 and a right medial segment 250, which are disposed in the right middle lobe 135. The right lower lobe 140 includes bronchopulmonary segments comprised of a right superior segment 260, a right medial basal segment (which cannot be seen from the lateral view and is not shown in FIG. 3), a right anterior basal segment 280, a right lateral basal segment 290, and a right posterior basal segment 295.

Figure 4:
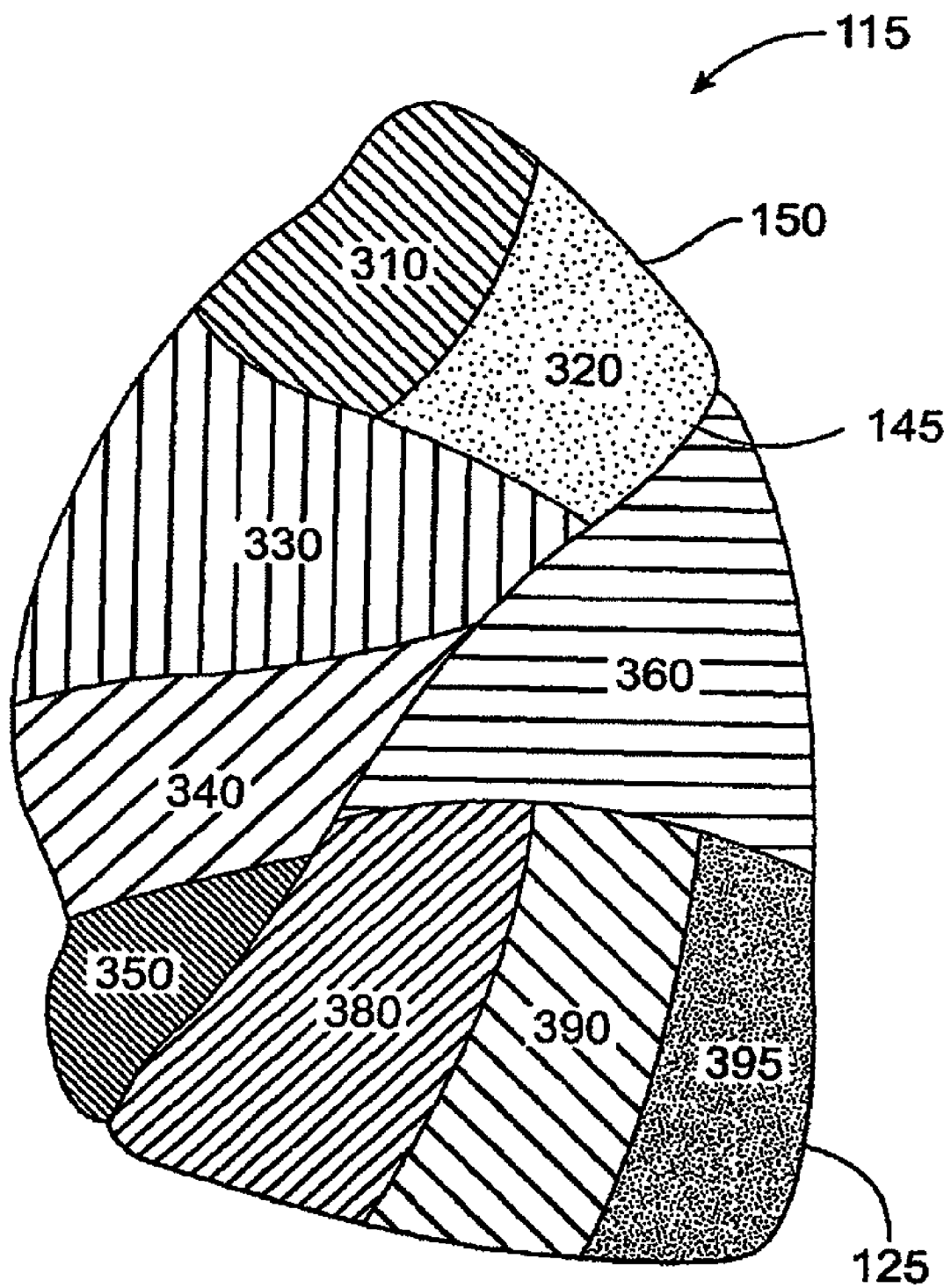
FIG. 4 shows a lateral view of the left lung.

FIG. 4 shows a lateral view of the left lung 115, which is subdivided into lung regions comprised of a plurality of bronchopulmonary segments. The bronchopulmonary segments include a left apical segment 310, a left posterior segment 320, a left anterior segment 330, a left superior segment 340, and a left inferior segment 350, which are disposed in the left lung upper lobe 150. The lower lobe 155 of the left lung 115 includes bronchopulmonary segments comprised of a left superior segment 360, a left medial basal segment (which cannot be seen from the lateral view and is not shown in FIG.

4), a left anterior basal segment 380, a left lateral basal segment 390, and a left posterior basal segment 395.

Figure 5:
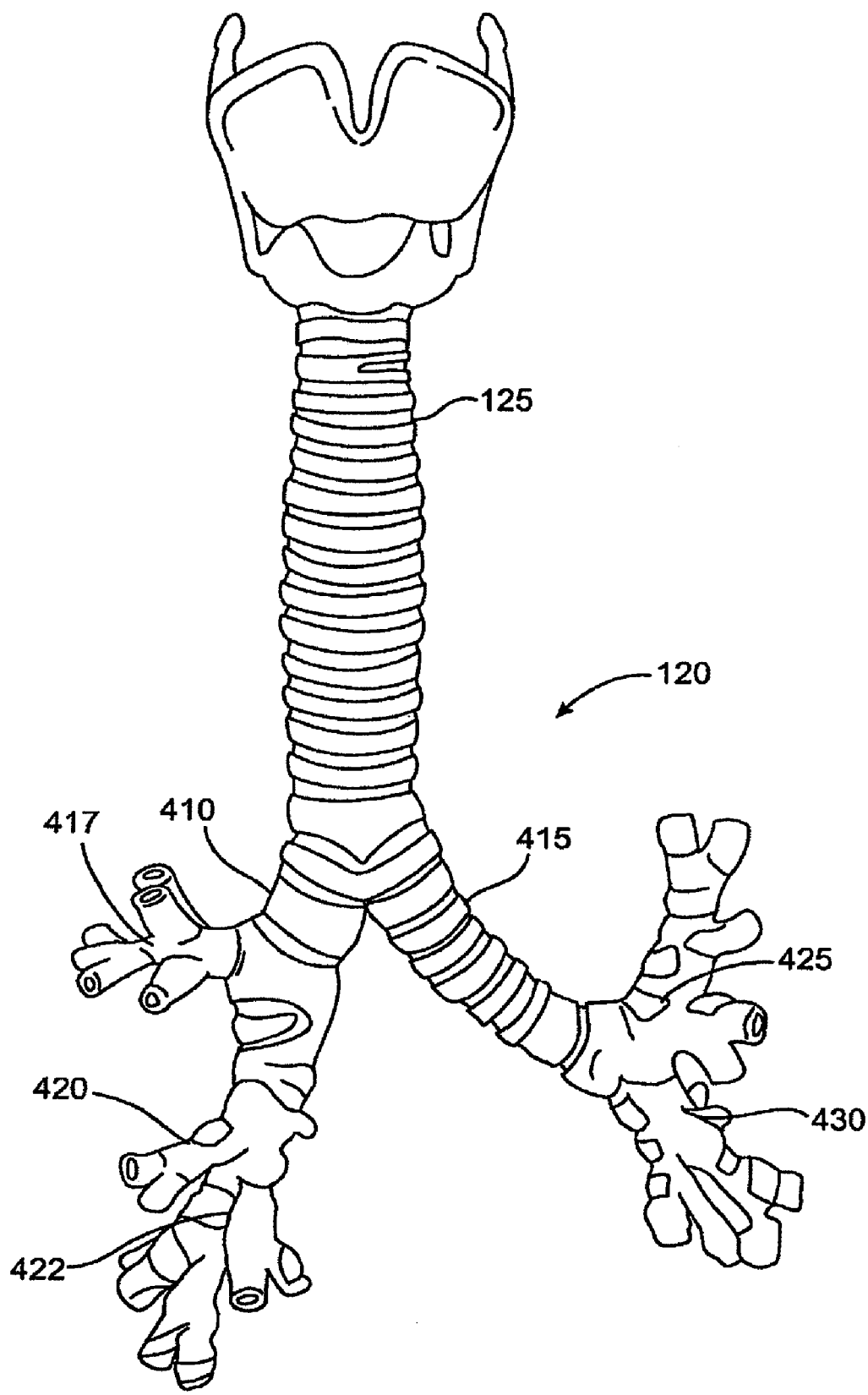
FIG. 5 shows an anterior view of the trachea and a portion of the bronchial tree.

FIG. 5 shows an anterior view of the trachea 125 and a portion of the bronchial tree 120, which includes a network of bronchial passageways, as described below. In the context of describing the lung, the terms "pathway" and "lumen" are used interchangeably herein. The trachea 125 divides at a lower end into two bronchial passageways comprised of primary bronchi, including a right primary bronchus 410 that provides direct air flow to the right lung 110, and a left primary bronchus 415 that provides direct air flow to the left lung 115. Each primary bronchus 410,415 divides into a next generation of bronchial passageways comprised of a plurality of lobar bronchi. The right primary bronchus 410 divides into a right upper lobar bronchus 417, a right middle lobar bronchus 420, and a right lower lobar bronchus 422. The left primary bronchus 415 divides into a left upper lobar bronchus 425 and a left lower lobar bronchus 430. Each lobar bronchus, 417, 420, 422, 425, 430 directly feeds fluid to a respective lung lobe, as indicated by the respective names of the lobar bronchi. The lobar bronchi each divide into yet another generation of bronchial passageways comprised of segmental bronchi, which provide air flow to the bronchopulmonary segments discussed above.

As is known to those skilled in the art, a bronchial passageway defines an internal lumen through which fluid can flow to and from a lung or lung region. The diameter of the internal lumen for a specific bronchial passageway can vary based on the bronchial passageway's location in the bronchial tree (such as whether the bronchial passageway is a lobar bronchus or a segmental bronchus) and can also vary from patient to patient. However, the internal diameter of a bronchial passageway is generally in the range of 3 millimeters (mm) to 10 mm, although the internal diameter of a bronchial passageway can be outside of this range. For example, a bronchial passageway can have an internal diameter of well below 1 mm at locations deep within the lung.

Figure 6:
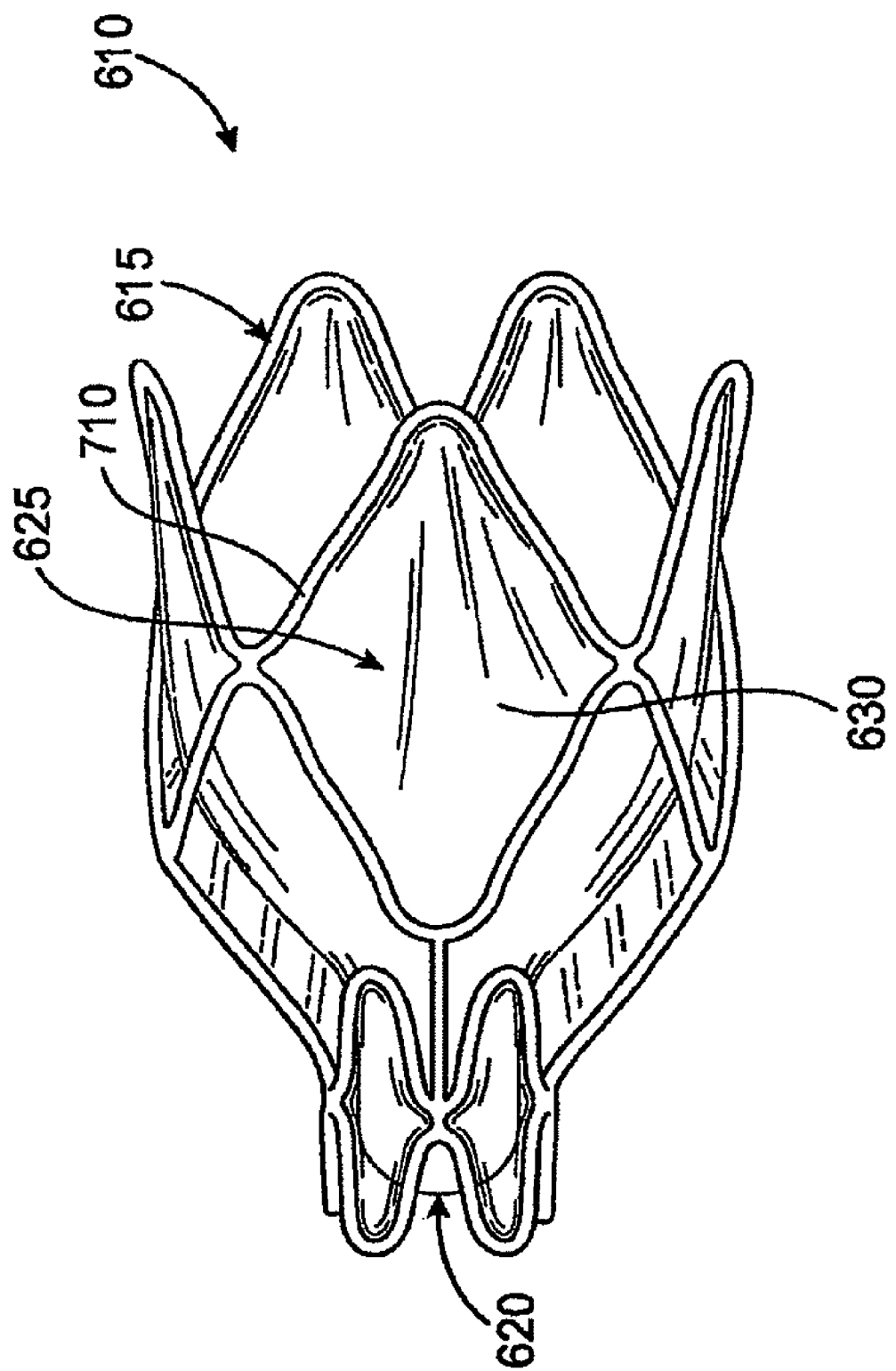
FIG. 6 shows a perspective view of a bronchial isolation device.

Bronchial Isolation Device. FIG. 6 shows a perspective view of a bronchial isolation device 610 that includes a frame 615, a valve member 620 mounted in the frame 615, and a membrane 625. As mentioned above, the bronchial isolation device 610 can be positioned within a bronchial passageway to regulate fluid flow through the bronchial passageway.

Figure 7:
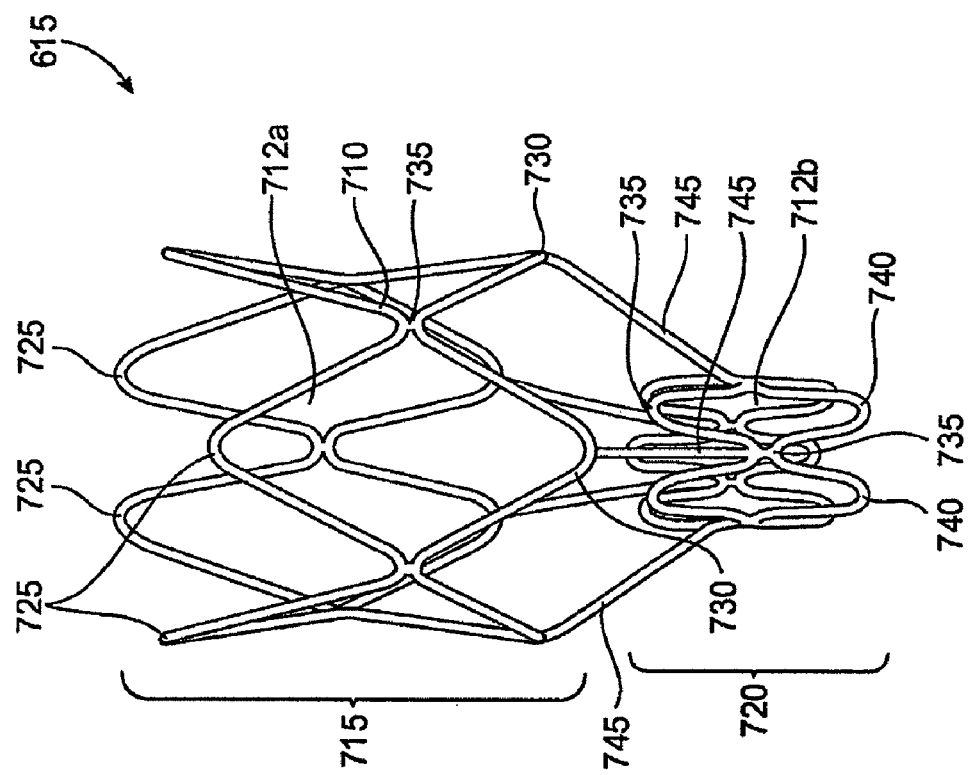
FIG. 7 shows a side view of a frame of the bronchial isolation device.
Figure 8:
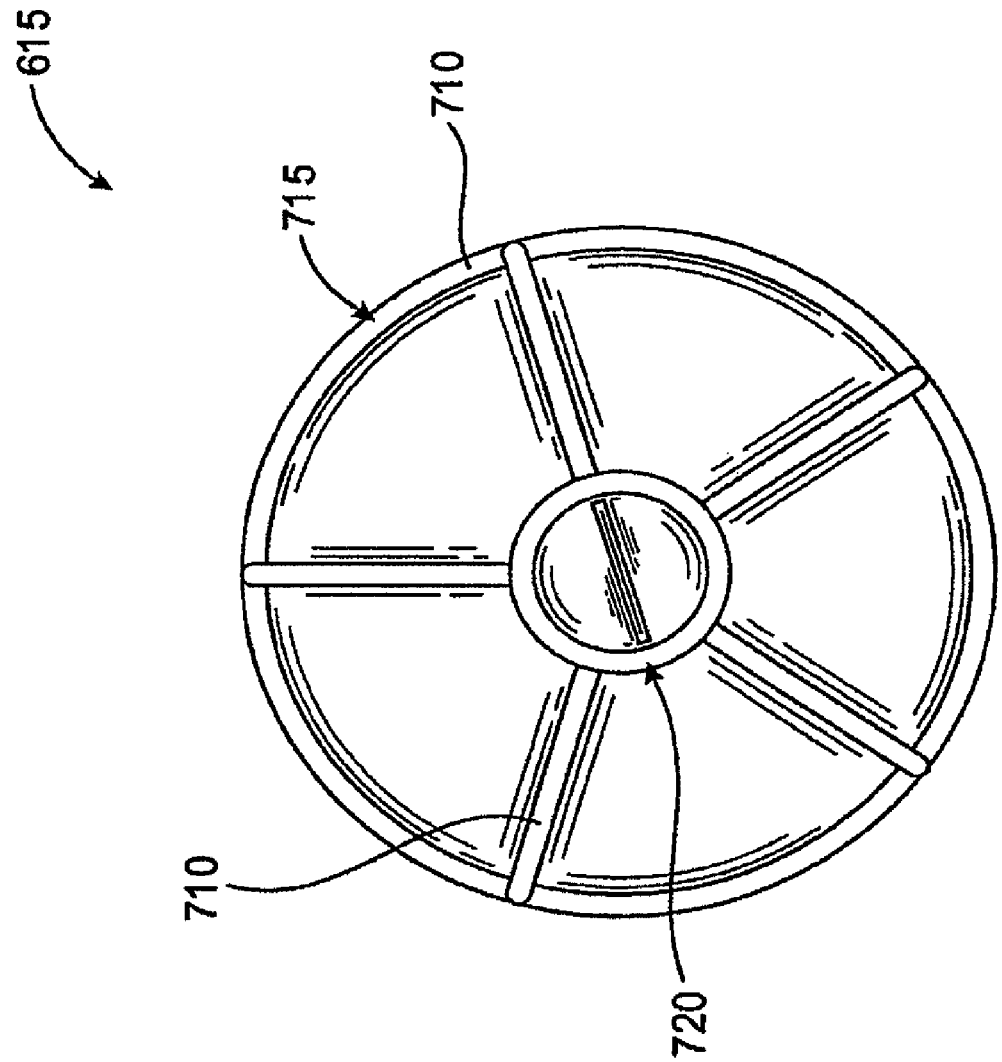
FIG. 8 shows a front view of the frame of FIG. 7.

Frame. FIG. 7 shows a side, perspective view of a first embodiment of the frame 615, which includes a retainer portion 715 and an integrally-connected valve protector portion 720. The frame 615 is comprised of a plurality of interconnected struts 710 that collectively form the outer periphery of the bronchial isolation device 610. As shown in the front view of FIG. 8, at least some of the struts 710 are collectively arranged in an annular configuration such that the shape of the frame 615 approximates the internal shape of a bronchial passageway.

With reference to FIG. 7, the struts 710 are arranged so as to form a plurality of diamond-shaped cells 712. The cells are referred to generally using the reference numeral 712. Cells within the retainer portion 715 are referred to as "retainer cells 712a" and cells within the valve protector portion 720 are referred to as "valve protector cells 712b." The cells 712 can vary in size and shape. For example, the retainer cells 712a are longer and wider in size than the valve protector cells 712b. It should be appreciated that the size, shape and quantity of the struts 710 and the cells 712 can vary. For example, the struts 710 can be arranged in a z-pattern or a "zig-zag" pattern.

The retainer portion 715 of the frame 615 has a diameter that is larger than the diameter of the valve protector portion 720. When the bronchial isolation device 610 is deployed within a bronchial passageway, the diameter of the retainer portion 715 is sufficiently large to cause the retainer portion 715 to press against and anchor to the walls of the bronchial passageway to secure the bronchial isolation device 610 in a fixed location relative to the bronchial passageway. Each retainer cell 712 of the frame 615 may be shaped to have a curved, distal edge 725 and a curved, proximal edge 730 that both assist in anchoring the retainer portion 715 to the bronchial passageway, as described more fully below. Each cell 712 is attached to an adjacent cell 712 at a cell junction 735.

With reference still to FIG. 7, the valve protector portion 720 has valve protector cells 712b, which are smaller than the retainer cells 712a of the retainer portion 715 in order to compensate for the smaller diameter of the valve protector portion 720. Each valve protector cell 712b may have a curved, distal edge 735 and a curved, proximal edge 740. As mentioned, the size and shape of the valve protector cells 712 and the retainer cells 712a can vary. The valve protector portion 720 at least partially surrounds the valve member 620 to maintain a default shape of the valve member, as described more fully below. The valve protector portion 720 can be rigid or flexible and it can be configured to collapse and expand.

A plurality of linking struts 745 connect the valve protector portion 720 to the retainer portion 715 of the frame 615. In the embodiment shown in FIG. 7, at least one linking strut 745 connects each retainer cell 712a to each valve protector cell 712b. In this regard, each linking strut 745 has a first end that connects to the curved, proximal edge 730 of a respective retainer cell 712a. Each linking strut 745 also has a second end that connects to a cell junction 735 between two valve protector cells 712b or to a distal point of a zig-zag strut of the valve protector portion 720. The linking struts 745 extend in a longitudinal direction from the valve protector portion 720 to the retainer portion 715. The linking struts 745 can be manufactured to be stiff or flexible.

The linking struts 745 curve radially outward from the valve protector portion 715 to provide the frame 615 with a smoothly-shaped transition between the retainer portion 715 and the valve protector portion 720 so as to eliminate sharp edges. As can be seen in FIG. 7, the linking struts 745 have a smooth, curved contour without sharp edges to lessen the likelihood of the frame 615 digging into the bronchial wall during removal of the bronchial isolation device 610. In particular, the connection between the curved, proximal edges 730 of the retainer cells 712a and the first end of each linking strut 745 eliminates the proximal edges 730 of the retainer cells 712a from hanging in midair, which reduces the likelihood of the proximal edges 730 digging into the bronchial wall during removal. The linking struts 745 also provide a structural connection between the retainer portion 715 of the frame 615 and the distal edges 730 of the retainer cells 712a. This allows the distal edges 730 of the retainer cells 712a to be radially constricted by pulling or constricting the valve protector cells 712b, which assists removal of the bronchial flow control device 610 from a bronchial passageway, as described in more detail below.

Figure 9:
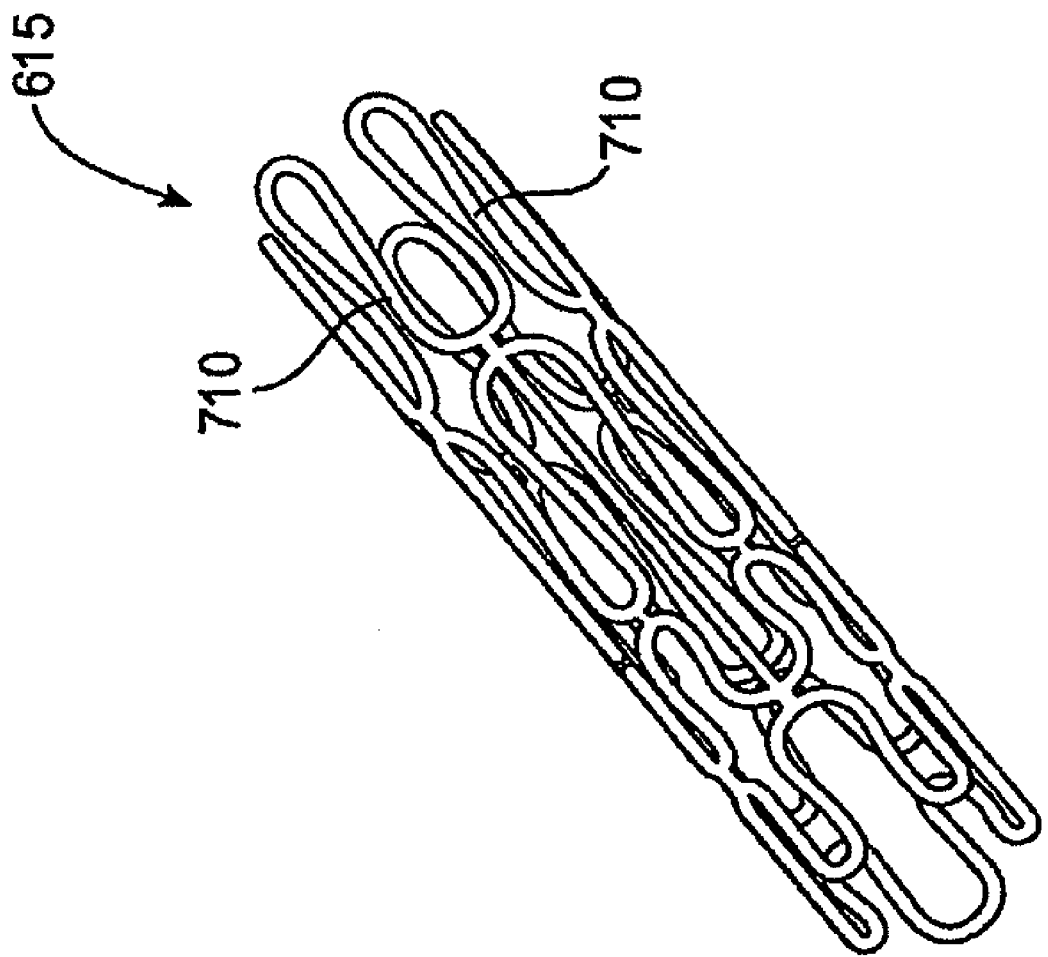
FIG. 9 shows the frame of FIG. 10 in a contracted state.

The frame 615 can transition between a contracted state and an expanded state. In the contracted state, the frame 615 has a diameter that is smaller than the diameter of the frame 615 in the expanded state. FIG. 9 shows a perspective view of another embodiment of a frame 615 in the contracted state, wherein the struts 710 form a series of undulating loops that can be, for example, in a zig-zag pattern. The struts 710 are arranged close to one another so that the cells 712 are constricted and the frame 615 has a reduced diameter. (The frame 615 in FIG. 9 is a different embodiment than the frame of FIG.

7. The frame 615 in FIG. 9 is the frame of FIG. 10 in a contracted state.) FIG. 7 shows the frame 615 in the expanded state, wherein the entire frame 615 is stretched radially-outward so that the struts 710 separate from one another to form enlarged cells 712. Thus, in the contracted state, the struts 710 can form at least two connected rows of undulating loops. The connected rows of undulating loops transition to diamond-shaped cells in the expanded state. It should be appreciated that the pattern of the struts can vary in both the contracted and expanded states.

During transition from the contracted state to the expanded state, the retainer portion 715 of the frame 615 radially expands to a larger diameter than the valve protector portion 720 so that the frame takes on the shape shown in FIG. 7. When the frame 615 is in the compressed state, the bronchial isolation device 610 has a compressed profile that facilitates insertion of the bronchial isolation device 610 into a delivery device, such as a bronchoscope, and also facilitates insertion into a bronchial passageway.

Various mechanisms can be employed to achieve the expanded and contracted states of the frame 615. In one embodiment, the frame 615 is manufactured of a malleable material. The frame 615 can be manually expanded to the anchoring state, such as by inserting an inflatable balloon inside the frame 615 once the bronchial isolation device 610 is implanted in the bronchial passageway, and then inflating the balloon to expand the frame beyond the material's yield point into an interfering engagement with the wall of the bronchial passageway.

Another mechanism that can be employed to achieve the two-state frame size is spring resilience. The insertion state can be achieved through a preconstraint of the frame 615 within the elastic range of the frame material. Once positioned in the bronchial passageway, the frame 615 can be released from constraint so that it spring resilience causes it to expand into an anchoring state. Constraining tubes or other mechanisms may achieve the initial insertion state.

Another mechanism that can be used to achieve both the contracted and the expanded states of the frame 615 is the shape memory characteristics of certain materials such as certain nickel titanium alloys, including Nitinol. The transition temperature of the frame 615 could be at a predetermined temperature, such as below body temperature. Under such a circumstance, a frame 615 that is at a temperature below the transition temperature can be deformed into a shape that is suitable for insertion, and will stay in this unrecovered state until the temperature is brought above the transition temperature. The unrecovered state of the frame 615 would be in an insertion position with the frame 615 having a smaller diameter. Upon recovery of the frame material, the frame 615 would expand, such as when the frame achieves a predetermined temperature within the bronchial passageway.

The frame 615 can be manufactured of a variety of biocompatible materials. In one embodiment, the frame 615 is manufactured of a superelastic material, such as Nitinol, that is heat-treated to attain the shape shown in FIG. 7. In one embodiment, the entire frame 615 is manufactured out of a single piece of tubing made out of Nitinol or some other material. FIG. 9 shows an isometric view of a tubular piece of material 1010 that has been cut into a pattern that forms the desired strut pattern. Once the material 1010 has been cut, such as through laser-cutting or chemical etching, the material 1010 is expanded and optionally heat treated so that it attains the shape shown in FIG. 10.

Alternatively, the frame may be manufactured from a flat piece of material that is cut into a pattern that forms the desired strut pattern, rolled into an annular configuration and then the mating edges are welded, bonded or otherwise joined. The material, as before, is then expanded and optionally heat treated so that it attains the shape shown in FIG. 10. It should be appreciated that the frame 615 can be manufactured of other materials, such as plastic or stainless steel.

Figure 10:
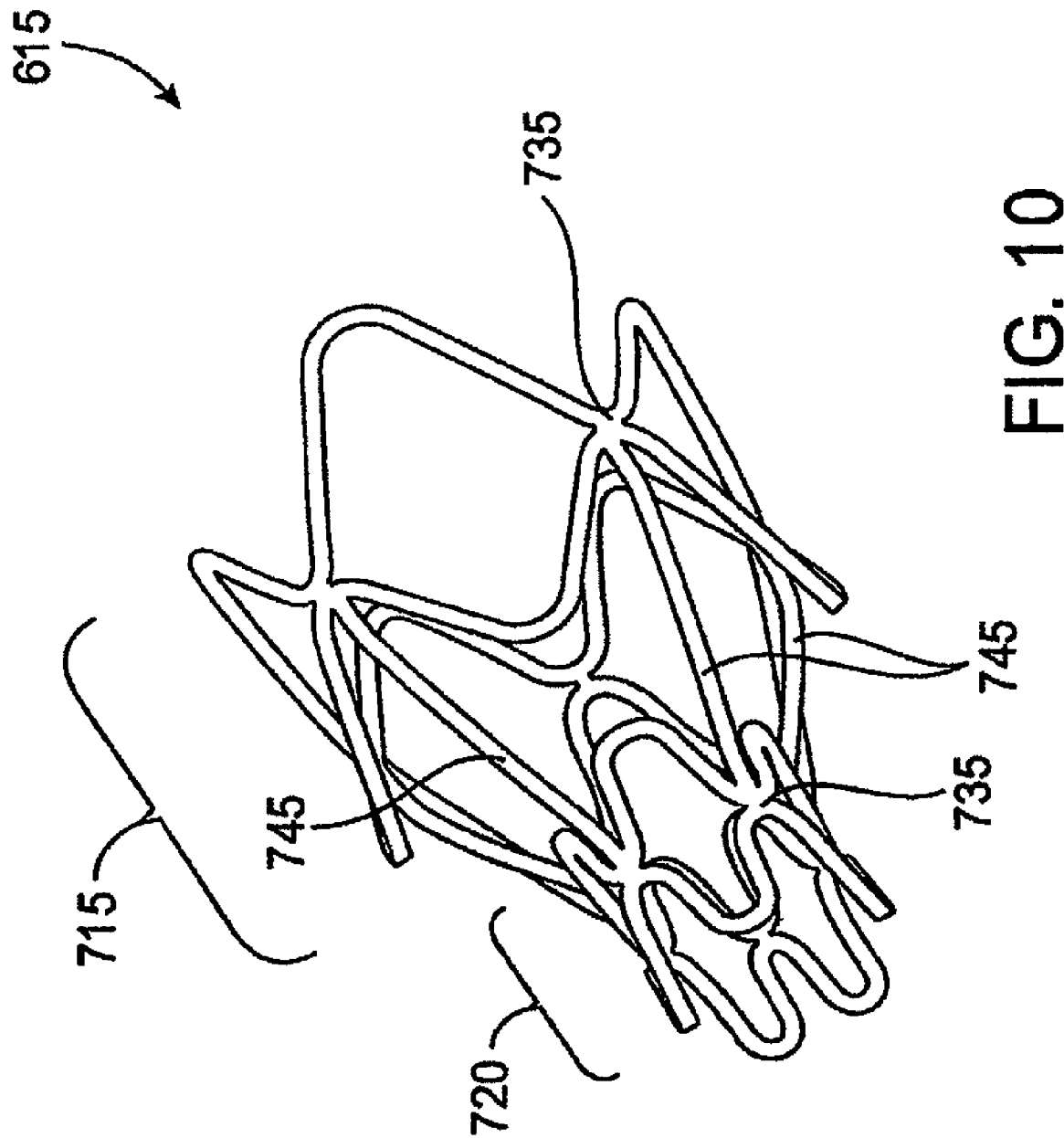
FIG. 10 shows another embodiment of the frame of the bronchial isolation device.

FIG. 10 shows a perspective view of another embodiment of the frame 615 wherein the linking struts 745 are connected to different locations on the retainer portion 715 and valve protector portion 720 of the frame. For each linking strut 745, the first end of the linking strut 745 is connected to the retainer portion 715 at the cell junction 735 between a pair of retainer cells 712*a*. The second end of the linking strut 745 is connected to a cell junction 735 between a pair of valve protector cells 712*b*. Thus, the curved, proximal edges 730 of the retainer cells 712*a* are cantilevered in that they are not connected to or supported by linking struts 745.

Figure 11:
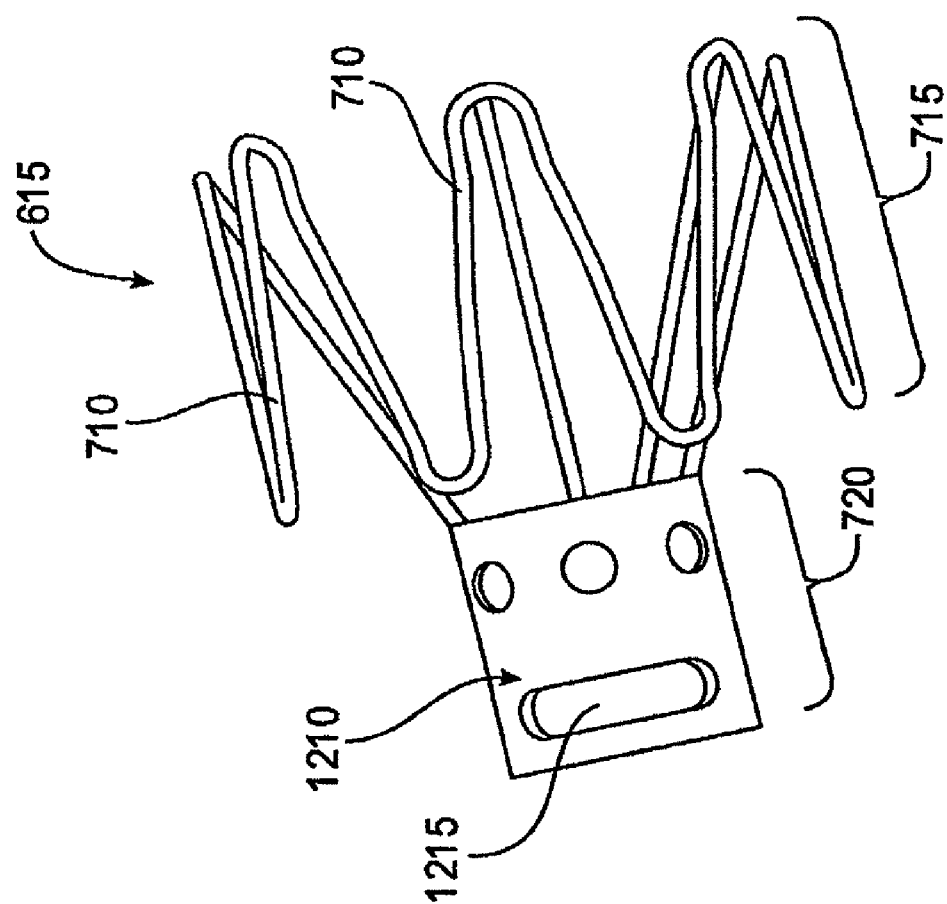
FIG. 11 shows another embodiment of the frame of the bronchial isolation device.

FIG. 11 shows yet another embodiment of the frame 615. In this embodiment, valve protector portion 720 of the frame 615 comprises a tube 1210 formed of a solid wall rather than a plurality of struts. The tube 1210 can include at least one removal window 1215 that can be grasped by a removal device (such as a set of jaws) during removal of the bronchial isolation device 610 from a bronchial passageway. The retainer portion 710 comprises a plurality of struts 710 that are shown arranged in a zig-zag pattern, although the struts 710 can also form cells, as in the previous embodiments, or can be in other patterns. The valve protector portion 720 comprised of the tube 1210 does not undergo any expansion or contraction, but rather retains its size. However, the retainer portion 715 can expand and contract as in the previous embodiments.

Figure 12:
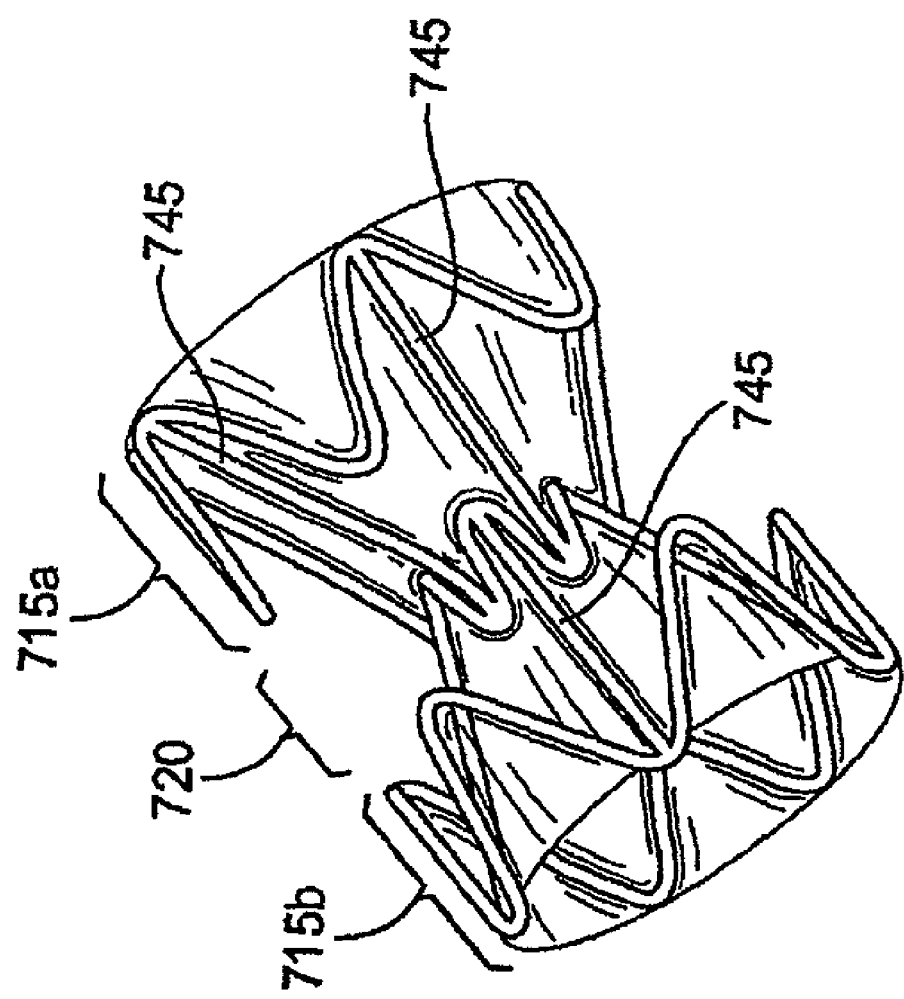
FIG. 12 shows another embodiment of a bronchial isolation device including a frame with dual retainer portions.

FIG. 12 shows another embodiment of the frame 615 (including the membrane 625) that includes two retainer portions including a proximal retainer portion 715*a* and a distal retainer portion 715*b*. A central valve protector portion 720 is disposed in-between the proximal retainer portion 715*a* and the distal retainer portion 715*b* and connected thereto by linking struts 745. The retainer portions 715*a,b* have larger diameters than the valve protector portion 720 so that the retainer 615 has an hourglass-like shape. It should be appreciated that the diameter of the proximal retainer portion 615*a* is not necessarily equal to the diameter of the distal retainer portion 615*b*.

The dual retainer portions 715*a*, 715*b* can provide an increase in stability when the bronchial isolation device 610 is mounted in a bronchial passageway, as both retainer portions 715*a*, 715*b* provide independent anchors to the bronchial wall. Both retainer portions 715*a*, 715*b* also provide seals against the bronchial wall in which the bronchial isolation device is mounted. Thus, if the anchor or seal in one of the retainer portions weakens or fails, the other anchor portion 715*a*, 715 can compensate for the weakened or failed seal.

It is important to prevent the bronchial isolation device from migrating in either the proximal or the distal direction after implantation in the bronchial passageway. It has been determined that migration in the proximal (i.e., exhalation) direction can occur when the patient coughs, resulting in pressure buildup behind the bronchial isolation device. This can lead to migration or expulsion of the device from the bronchial passageway. One mitigating factor that can reduce the likelihood of this occurring is that the bronchial passageways are constricted by the pressure of the cough, and this can cause the passageway to tend to grip the device more firmly in place. In addition, exhalation is inherently difficult for patients with emphysema, and has the effect of reducing the pressure that can build up behind the device during exhalation. In addition, the exhalation flow produced by coughing or breathing will preferentially flow through the valve, and will thus reduce the pressure that can build up behind the device. Migration in the distal (i.e., inhalation) direction can occur when the patient takes a deep inhalation breath, which can result in the device being "sucked" deeper into the lung. This effect is exacerbated by the fact that the bronchial lumens expand when air is inhaled, and this can lead to a less secure retention of the device in the airway. In view of the foregoing, it is desirable to have features on the frame 615 to prevent or limit migration of the device after implantation, such as to prevent or limit migration in the distal direction.

Figure 13:
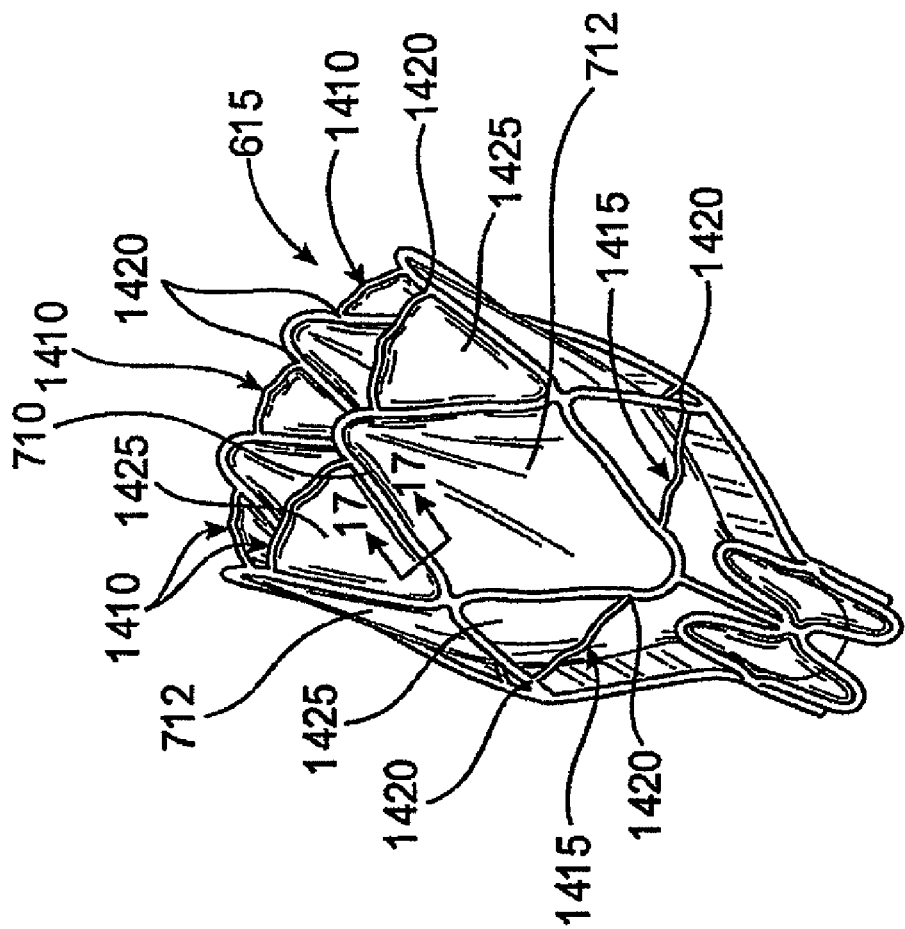
FIG. 13 shows an embodiment of the frame with cross struts, the frame in an expanded, annular state.

FIGS. 13-16 show embodiments of the frame 615 that include features that prevent or limit migration of the device in the proximal or distal direction once the device is implanted in a bronchial passageway. In one embodiment, the frame 615 includes retention prongs comprised of cross struts that resist migration of the bronchial isolation device in a bronchial passageway, such as by limiting the depth that the cell portions of the frame can penetrate into a bronchial wall in which the bronchial isolation device 610 is located. FIG. 13 shows the frame 615 in an expanded, annular state, wherein the frame includes at least one distal cross strut 1410 and at least one proximal cross strut 1415. The cross struts 1410, 1415 comprise additional struts or projections that have v-shape in the expanded state and extend outward between the struts of the frame 615. The cross struts 1410, 1415 can be loop shaped in the contracted state. The cross struts 1410, 1415 extend outward from the cells 712 at connection locations 1420, which serve as stopping points that limit the cells 712 from penetrating into a bronchial wall beyond a predetermined distance, as described in more detail below. The cross struts 1410, 1415 also form additional cells 1425 that can be engaged with the membrane 625 to provide additional sealing capability between the frame 615 and the bronchial wall. It should be appreciated that the cross struts 1410, 1415 can be positioned at various locations on the frame beside that which is shown in FIG. 13.

Figure 14:
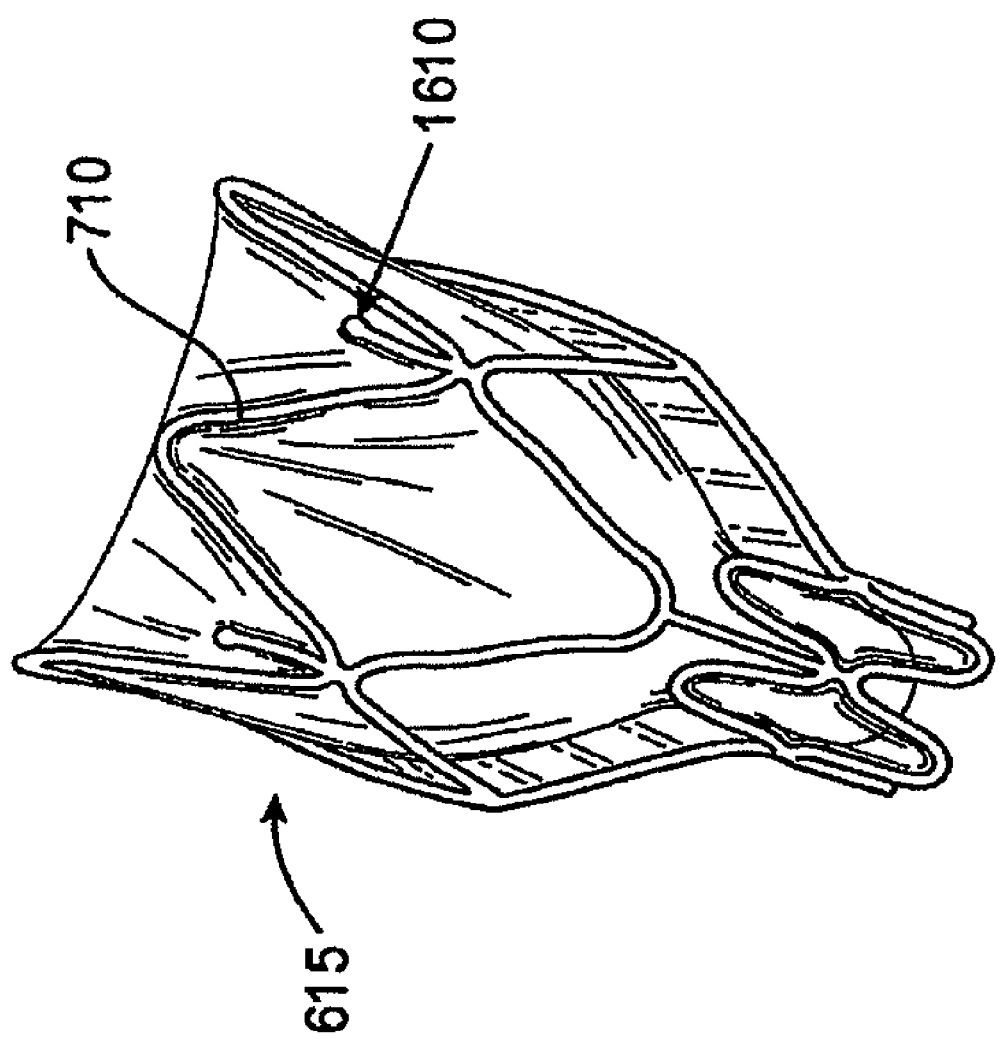
FIG. 14 shows another embodiment of the frame with retention prongs.

FIG. 14 shows another embodiment of the frame 615 with retention prongs 1610 that project radially-outward from the struts 710 in the expanded state. The prongs 1610 are bent so that they protrude radially-outward from the radial periphery of the retainer portion of the frame 615. When the bronchial isolation device 610 is implanted in a bronchial passageway, the prongs 1610 can at least partially sink in the bronchial wall tissue and prevent migration of the device in the distal direction. Unlike the distal cross struts 1410 that limit migration in the distal direction by limiting the depth of penetration of the cells 712, the retention prongs 1610 limit migration in the distal direction by fixing the frame 615 to the bronchial wall and thus preventing the cells 712 from penetrating the bronchial wall tissue.

Figure 16:
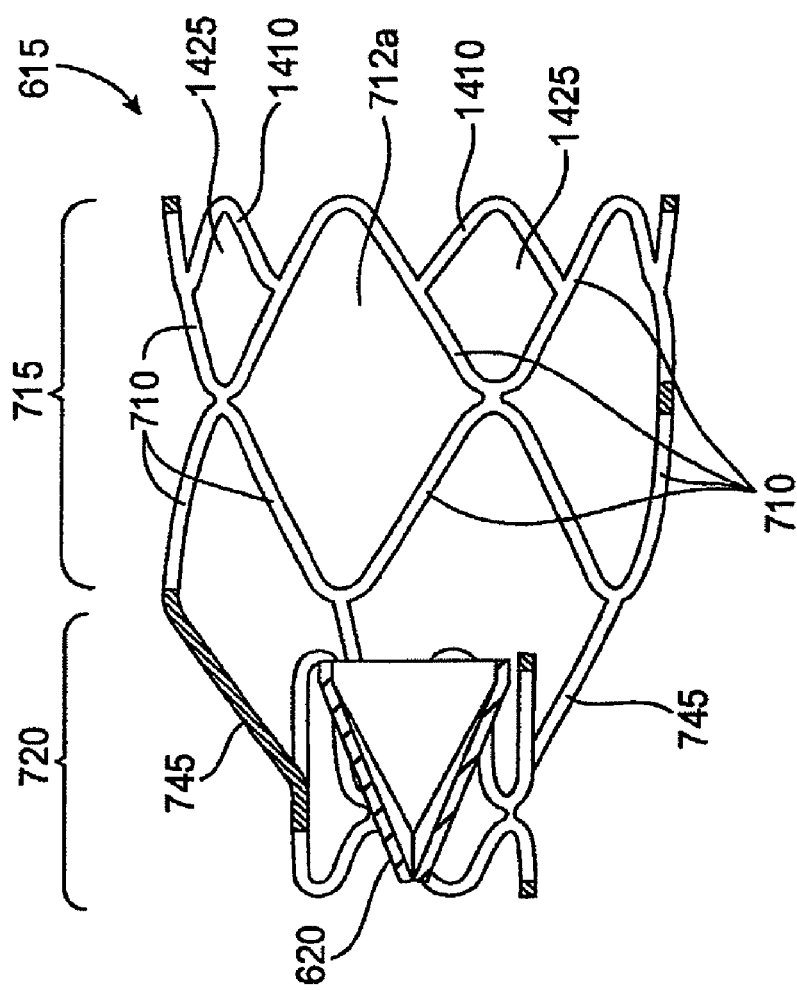
FIG. 16 shows a cross-sectional, side view of the frame of FIG. 16 along line 16-16 of FIG. 15.
Figure 15:
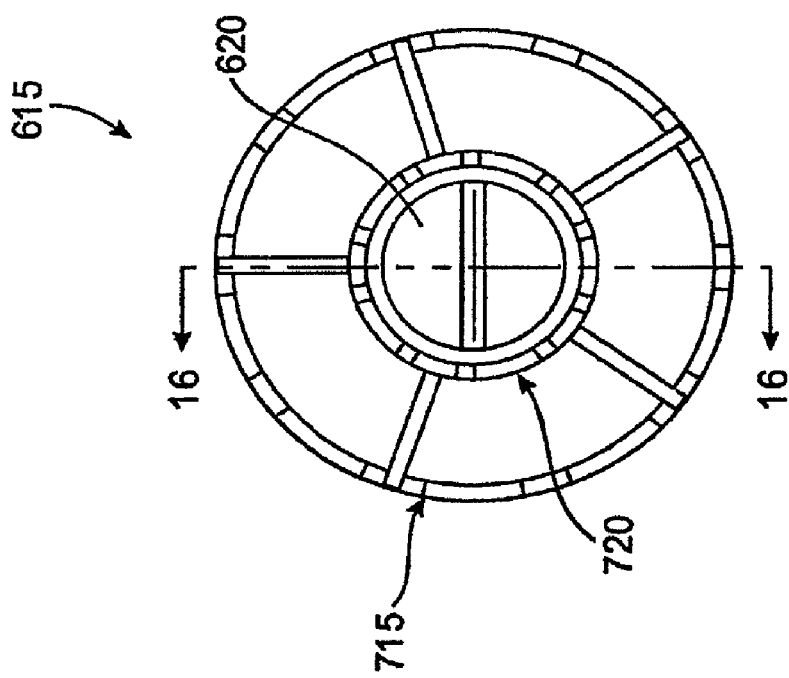
FIG. 15 shows a front view of another embodiment of the frame.

With reference to FIGS. 15 and 16, there is shown another embodiment of the frame 615. FIG. 15 shows a front view of the frame 615 and FIG. 16 shows a cross-sectional view of the frame 615. The valve member 620 is shown in FIG. 16 mounted within the valve protector portion 720. FIG. 16 does not show the membrane 625 for clarity of illustration, although it should be appreciated that the membrane 625 would be attached to the frame 615 and the valve member 620 and would thereby secure the valve member 620 to the frame 615. The frame 615 includes distal cross struts 1410 that form distal cells 1425 that can be smaller than the retainer cells 712a. The cells 1425 can move and flex independently of the retainer cells 712a that form the remainder of the retainer section 715 of the frame 615. This allows different portions of the retainer sections to independently conform to the shape of a bronchial wall.

Figure 17A:
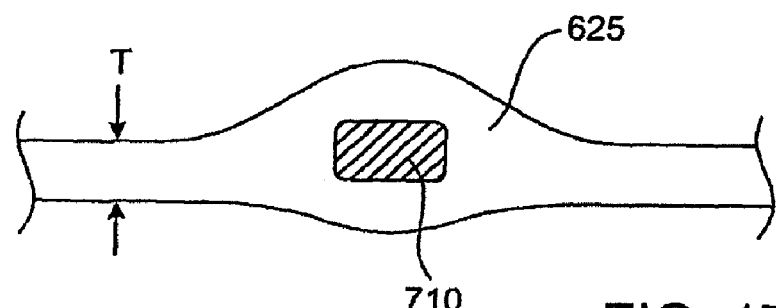
FIG. 17A-17D each show a cross-sectional view of a portion of a frame strut and an embodiment of the membrane of the bronchial isolation device, the view along the line 17-17 of FIG. 13.

Membrane. With reference again to FIG. 13, the membrane 625 is connected to the 5 frame 615. FIG. 17A shows a cross-sectional view of a portion of the membrane 625 and a strut 710, cut along the line 17-17 of FIG. 13. As shown in the embodiment of FIG. 17A, the membrane 625 can fully encapsulate the struts 710 of the frame 615 so that the membrane 625 is integrally attached to the frame 615. The encapsulation of the membrane 625 over the struts 710 can be accomplished by using a dipping manufacturing process described below. The membrane 625 can also be connected to the valve member 620.

As shown in FIG. 13, the membrane 625 extends in a web-like manner between the struts 710 within the spaces of the cells 712 of the frame 615. The membrane 625 can be stretched in tension across the cells, although this is not necessary. As shown in FIG. 17A, the membrane has a thickness T. The membrane 625 generally bulges outwardly from the struts 710 in the region where the membrane 625 surrounds the struts. In one embodiment, the thickness T is not substantially larger than the diameter or thickness of the struts 710. In this manner, the membrane 625 does not substantially contribute to or increase the diameter of the frame 615. The membrane 625 can be disposed over the entire frame 615, including both the retainer portion 715 and the valve protector portion 720, or the membrane can be disposed only over a portion of the frame, such as the enlarged-diameter retainer portion 715. It should be appreciated that the thickness T of the membrane can vary relative to the diameter of the struts 710 and that the thickness T need not be uniform across the entire membrane.

Figure 17B:
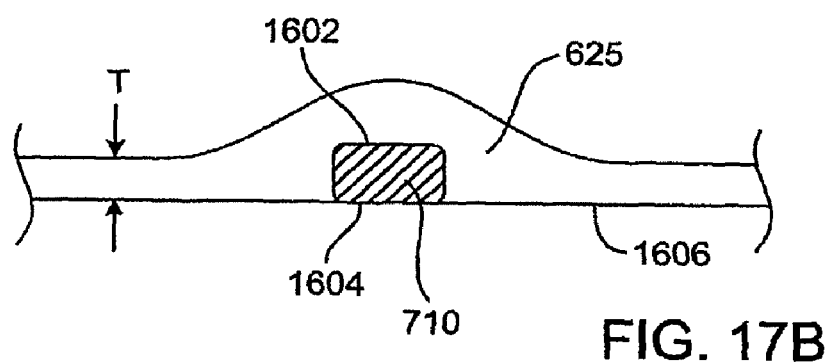

FIG. 17B shows another embodiment of the configuration of the membrane 625 relative to the struts 710. In this embodiment, the membrane 710 does not entirely encapsulate the strut 710 but rather leaves a portion of the strut 710 uncovered or exposed. In this regard, the membrane 710 covers a radially outward portion 1602 and sides of the strut 710 and does not cover a radially inward portion 1604 of the struts 710. An inner surface 1606 of the membrane 625 is positioned substantially flush with the radially-inward portion 1604 of the strut 710, thereby leaving the radially-inward portion 1604 exposed.

Figure 17C:
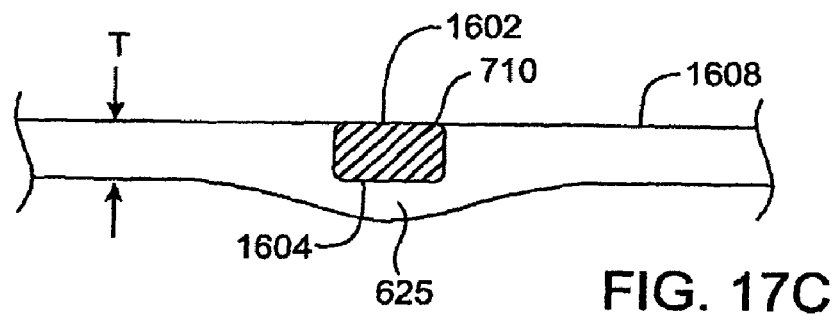

FIG. 17C shows another embodiment of the configuration of the membrane 625 relative to the strut 710 wherein the membrane 625 does not entirely encapsulate the strut 710. In this embodiment, the membrane covers the radially-inward portion 1604 but does not cover the radially-outward portion 1602 of the strut 710. An outer surface 1608 of the membrane 625 is positioned substantially flush with the radially-outward portion 1602 of the strut 710, thereby leaving the radially-outward portion 1602 exposed.

Figure 17D:
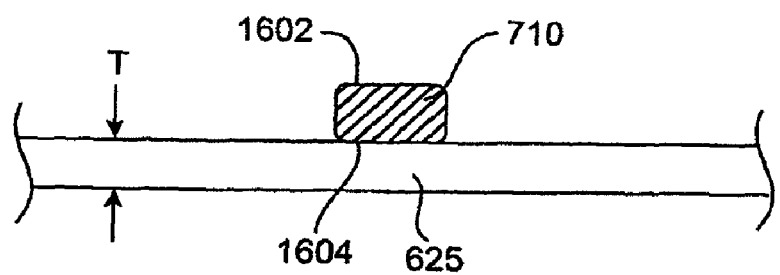

FIG. 17D shows yet another embodiment of the configuration of the membrane 625 relative to the strut 710. In this embodiment, the membrane 625 is mounted on one side of the strut 710 and does not encapsulate or surround the strut 710. FIG. 17D shows the membrane 625 mounted on the radially-inward portion 1604 of the strut 710 with the outer surface 1608 of the membrane juxtaposed with the radially-inward portion 1604. It should be appreciated that the membrane 625 can also be mounted on the radially-outward portion 1602. Furthermore, it should be appreciated that the membrane 625 can be mounted on the struts 710 in other manners and that the membrane 625 can encapsulate other portions of the struts and leave various portions of the struts 710 uncovered or exposed.

In one embodiment, the membrane 625 is disposed over the entire retainer portion of the frame 615 such that the retainer portion can expand and contract without causing the membrane 625 to wrinkle against the bronchial wall when disposed in a bronchial passageway. The membrane 625 can be thin and elastic so that the membrane 625 can expand along with the frame 615 without inhibiting the frame from exerting a sufficient radial force to grip the bronchial wall. Thus, the membrane 625 does not inhibit the frame 615 from expanding or contracting, but rather expands and contracts according to any expansion or contraction of the frame 615.

The membrane 625 is desirably attached to the valve member 620 in a leak-free manner. That is, when the bronchial isolation device 610 is positioned in a bronchial passageway, fluid is prevented from flowing in-between the membrane 625 and the valve member, but must rather flow through a fluid-flow opening in the valve member 620. In this regard, the membrane 625 provides a fluid pathway into an entry mouth of the valve member that directs fluid in a bronchial passageway into the valve member, as described more fully below. It is not necessary that the membrane 625 completely cover the self-expanding valve protector section of the frame or that the membrane 625 completely cover the valve member 620.

The membrane 625 is firmly attached to the self-expanding, retainer portion 715 of the frame 615. When the bronchial isolation device 610 is properly positioned within a bronchial passageway, the self-expanding retainer portion 715 radially expands to sealingly anchor against the bronchial passageway wall. It should be appreciated that the seal can be either between the membrane 625 and the bronchial wall or the frame 615 and the bronchial wall, as described more fully below. Thus, the bronchial isolation device 610 seals inside the bronchial passageway, and flow of fluid around the bronchial isolation device 610 is prevented in a desired direction, such as the inhalation direction or in the exhalation direction. In general, the bronchial isolation device 610 also prevents flow around the device in the exhalation direction, and the only flow that is allowed is through the valve member 620 in the exhalation direction. However, the self-expanding retainer portion 715 of the frame 615 can be configured to allow fluid flowing in the exhalation direction to flow between the frame and the bronchial lumen wall as well as through the one-way valve, yet still prevent flow in the inhalation direction (either through the one-way valve or between the frame and the bronchial lumen wall).

The flexible membrane 625 can be thin so that it provides a relatively small amount of material that must be compressed when the bronchial isolation device 610 is in the compressed state. In one embodiment, the membrane 625 is contoured so as to increase the tendency of the membrane 625 to deform in a desired manner when the flow control device 610 is compressed. The thickness of the membrane 625 can vary. In one embodiment, the membrane 625 has a thickness in the range of about 0.0005 inch to about 0.005 inch, although other thickness outside this range are possible. In one embodiment, the membrane 625 has a thickness in the range of about 0.001 inch to about 0.010 inch. In one embodiment, the thickness of the membrane is 0.003 inch.

The flexible membrane 625 is formed of a biocompatible, flexible material, such as, for example, silicone, urethane, or a urethane/silicone composite. It should be appreciated that the membrane can be manufactured of other materials.

The thin membrane 625 can be manufactured according to a variety of processes. In an exemplary process, described with reference to FIG. 18, the membrane 625 is manufactured by dipping a frame 615 into a dispersion 1810 of material used to manufacture the membrane 625. The dispersion 1810 is located within a container 1815. According to the exemplary process, the frame 615 is first expanded, such as to the maximum possible diameter. This may be accomplished, for example, by mounting the frame 615 onto a mounting tool, such as a mandrel 1820 that is sized to receive the frame 615. The frame 615 is then dipped into the dispersion 1810, such as in a dispersion of silicone, polyurethane or other polymer. In one exemplary embodiment, the dispersion 1810 is generated by mixing platinum cure silicone (uncured) with xylene. Another exemplary dispersion 1810 comprises polyurethane dissolved in a solvent such as THF (tetrahydrofuran) or DMAC (dimethyl acetamide).

When the frame 615 is dipped into the dispersion 1810, the material of the dispersion adheres to the frame 615. The adhesion of a polymeric dispersion to a Nitinol frame can be enhanced with a primer such as a naphtha solution, which is especially useful for silicone membranes. After dipping the frame 615, the frame 615 is removed from the dispersion so that a portion of the dispersion adheres to the frame 615. The dispersion is then allowed to cure and form the membrane 625.

Figure 18:
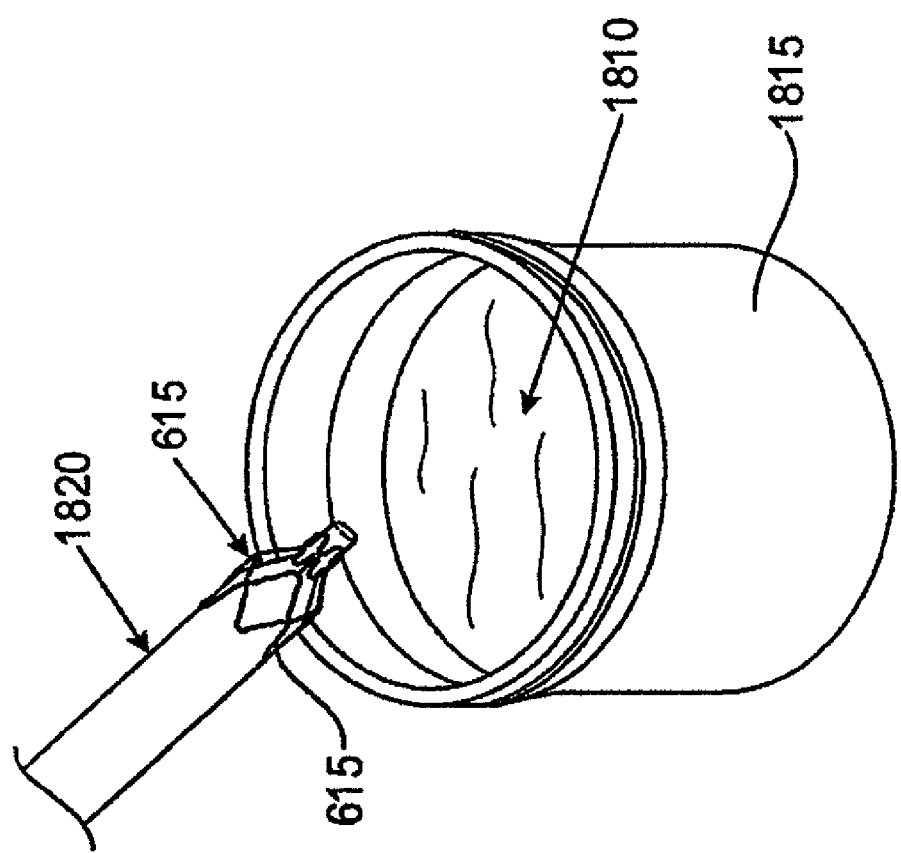
FIG. 18 shows a step in the process of forming a membrane on the frame of the bronchial isolation device.

The thickness of the membrane 625 can be controlled by adjusting the percent solids of the dispersion and the dip rate, or through the use of a dipping mandrel, such as the mandrel 1810 shown in FIG. 18. In one embodiment, the dipped frame 615 is rotated during the cure process about an axis that is either in a vertical orientation, a horizontal orientation, or both. The rotation of the frame 615 uniformly coats the dispersion about the frame 615. A variety of membrane thicknesses can be achieved using this process.

Figure 20:
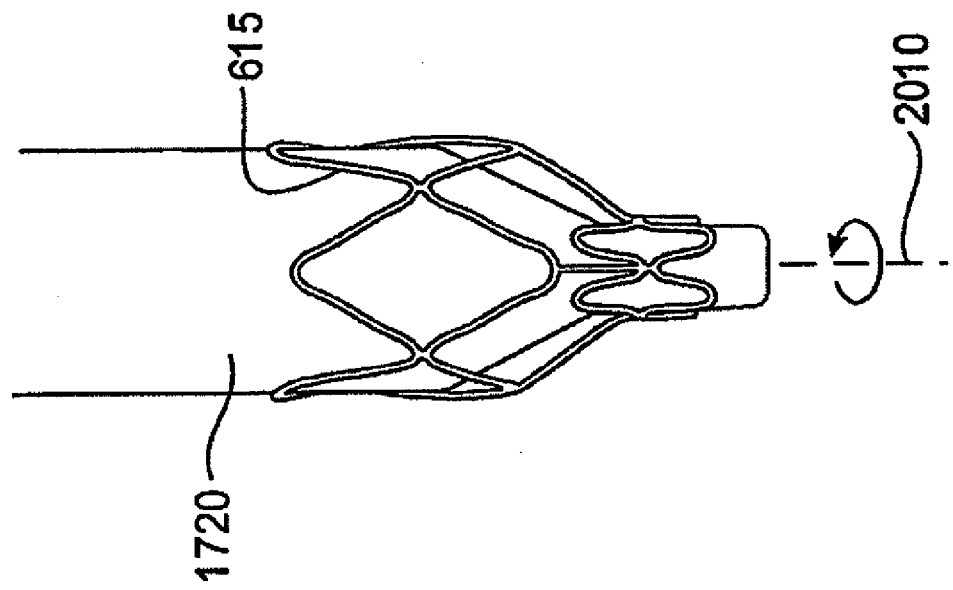
FIG. 20 shows another step in the process of forming a membrane on the frame of the bronchial isolation device.
Figure 19:
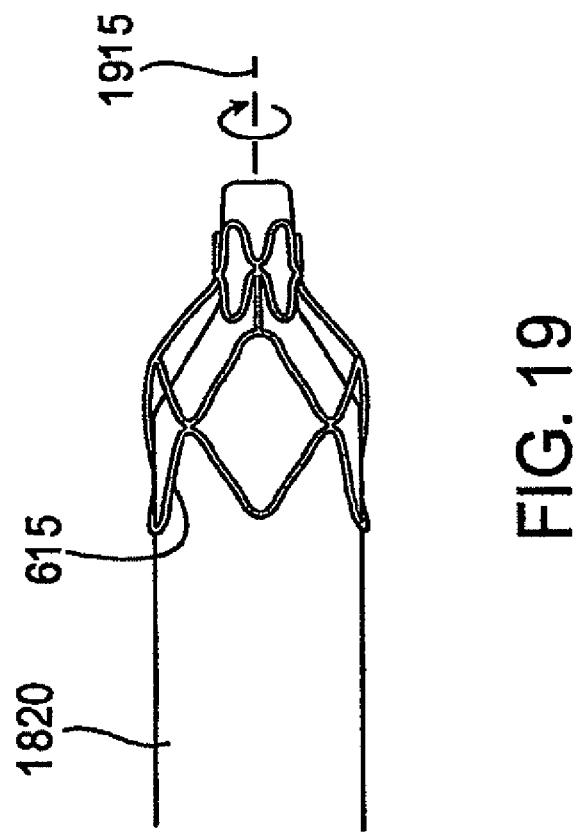
FIG. 19 shows another step in the process of forming a membrane on the frame of the bronchial isolation device.

One specific method of applying the dispersion 1810 to the frame 615 is to dip the frame 615 into the dispersion 1810 (such as silicone), rotate the frame 10 615 to a horizontal position, and spin the frame 615 about a horizontal axis 1915 to evenly distribute the dispersion 1810 about the frame 615, as shown in FIG. 19. After a period of time, such as about three minutes, the frame 615 is rotated to a vertical position that is upside down relative to the original dipped position, and spun about a vertical axis 2010 to continue to evenly distribute the dispersion, as shown in FIG. 20. The silicone can then be cured in an oven. One curing method includes a two stage cure. In the first stage, the silicone is cured at a first temperature for a first amount of time, such as at 140° F. for 10 minutes. In the second stage, the silicone is cured at a second temperature for a second amount, such as at 325° F. for 10 minutes.

As mentioned, the membrane 625 can have a contoured shape that increases the tendency of the membrane to deform in a desired manner when the flow control device is compressed. The contours on the membrane 625 can be created by dipping a stent that has a number of closed cells or perimeters, such as the cells 712. The dispersion fills the cells and creates a surface tension within the cells, which creates a dispersion membrane across each closed perimeter so that the membrane solidifies upon curing. The membrane contours can be altered by conducting the dipping process with the stent placed over a formed tool or mandrel 1820. In one embodiment, the mandrel 1820 is manufactured of a material that does not adhere to the dispersion, such as PFA or some other fluoropolymer, in order to eliminate or reduce adhesion of the membrane 625 to the mandrel 1820. By using this method, the shape of the membrane 625 can be altered when the frame 615 is compressed for delivery. For example, the mandrel 1820 can be contoured to create concave surfaces on the membrane, wherein the concave surfaces will pleat inward during compression of the frame 615. This protects the membrane during compression, loading, and deployment of the bronchial isolation device.

In the embodiment shown in FIG. 6, the membrane 625 does not extend distally or proximally past the frame 615.

Figure 22:
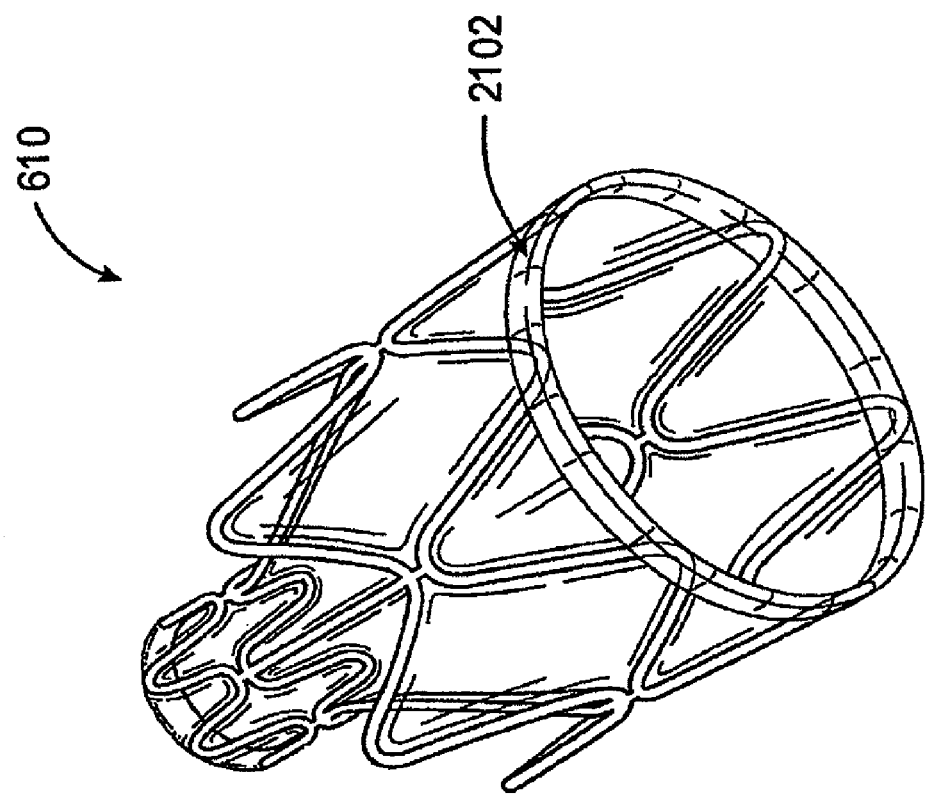
FIG. 22 shows an embodiment of the flow control device having a reinforced membrane edge.
Figure 21:
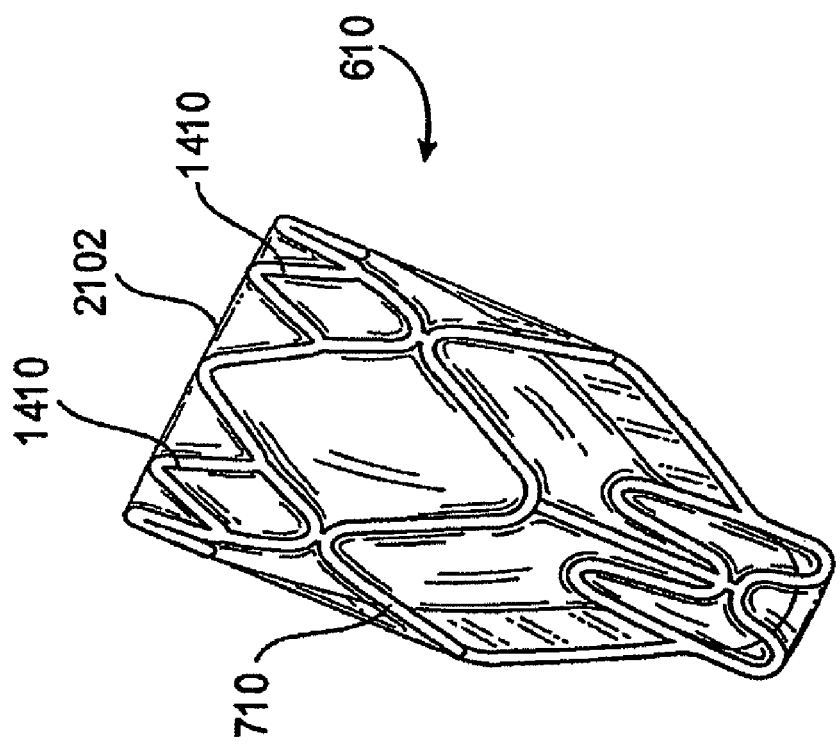
FIG. 21 shows an embodiment of the flow control device having an untrimmed membrane edge.

That is, the membrane 625 is trimmed so that its distal edge follows the contours of the distal-most struts 710. In another embodiment, shown in FIG. 21 using the embodiment of the frame of FIGS. 15 and 16, the membrane 625 extends distally past the struts 710 such that the membrane 625 has an untrimmed, distal edge 2102. In another embodiment of the untrimmed-membrane, shown in FIG. 22, the distal edge 2102 is folded over and bonded to itself to form a flap. It can be folded over either inside or outside of the membrane 625. The folded-over flap provides a thicker distal edge 2102 to reinforce the structural integrity of the distal edge 2102. Alternately, the distal edge 2102 can be structurally-reinforced by dipping the distal edge 2102 into a dispersion of the membrane material or by applying a section of the material to the distal edge 2102 with a syringe, and then curing the membrane 625 to form a reinforcing bead on the distal edge 2102.

Valve Member. With reference to FIG. 6, the valve member 620 is disposed within the valve protection portion 720 of the frame 615. The valve member 620 can be configured to either permit fluid flow in two directions (i.e., proximal and distal directions), permit fluid flow in only one direction (proximal or distal direction), completely restrict fluid flow in any direction through the bronchial isolation device 610, or any combination of the above. The valve member 620 can be configured such that when fluid flow is permitted, it is only permitted above a certain pressure, referred to as the cracking pressure. The valve member 620 is desirably formed of an elastic, biocompatible material, such as silicone, although other materials can be used.

When the valve member 620 comprises a one-way valve, it desirably has the following characteristics: low cracking pressure, high flow in the forward direction, rapid closure upon flow reversal, and complete sealing in the reverse direction, as discussed below.

Low Cracking Pressure. During exhalation from a lung that is damaged by emphysema or COPD, the amount of driving pressure that can be generated to force air out of the lung is quite low. Given this condition, in order for air to be exhaled from the isolated lung region, it is desirable that the cracking pressure in the exhalation direction be as low as possible. In one embodiment, the cracking pressure is in the range of 0 to 10 inches of water. In another embodiment, the cracking pressure is in the range of 0 to 5 inches of water. In another embodiment, the cracking pressure is in the range of 0 to 2 inch of water. Given the 100% humidity conditions that exist in the lungs, these cracking pressures can be measured under similar or wet conditions in order to simulate the conditions of the lungs.

High Flow Rate in the Forward Direction. Rapid exhalation of air from the region of the lung isolated behind a one-way or two-way valve device is important for the rapid and complete collapse of the isolated lung portion, or for the maximal improvement in flow dynamics in the absence of collapse. Thus, the higher the flow through the bronchial isolation device at a given pressure across the device, the better the performance of the device. To this end, in one embodiment, the pressure differential across the valve at a flow of 50 ml/min in the exhalation direction is in the range of 0 to 4 inches of water. In another embodiment, the pressure differential across the valve at a flow of 50 ml/min in the exhalation direction is in the range of 0 to 2 inch of water. In another embodiment, the pressure differential across the valve at a flow of 50 ml/min in the exhalation direction is in the range of 0 to 1 inches of water.

Rapid Valve Closure When Flow is Reversed. The responsiveness of the valve is a measure of how quickly the valve closes once flow through the valve in the exhalation direction is stopped. For example, a high-performing valve would close instantly when the valve encounters a reverse-direction flow and not allow any flow in the reverse direction back through the valve. When a flow of 120 ml/min is sent in the exhalation direction of the valve, and then reversed to flow in the inhalation direction, the valve closes and seal completely in less than 4 seconds in one embodiment, in less than 2 seconds in another embodiment, and in less than 1 second in another embodiment.

Complete Sealing of Valve in Reverse Direction. It is desirable for implanted one-way valve bronchial isolation devices to seal completely in the inhalation direction at all times after deployment in a bronchial passageway under all conditions. The valve desirably stays sealed regardless of the orientation of the patient's body, regardless of the rotational orientation of the valve in the bronchial lumen, regardless of whether or not the implanted device is being compressed by external compression of the bronchial lumen, regardless of whether or not there is mucus present on the valve seal surfaces, etc. In addition, the valve should remain sealed even if there is little or no pressure differential across the valve.

Figure 25:
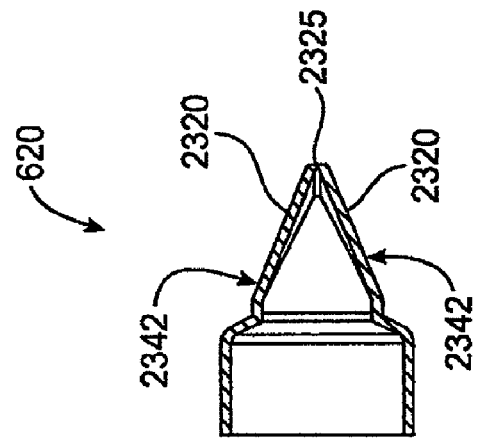
FIG. 25 shows a cross-sectional, side view of the duckbill valve member of FIG. 23.
Figure 24:
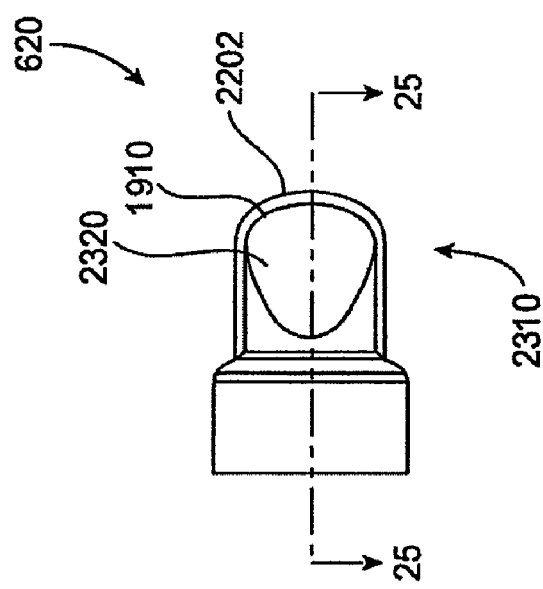
FIG. 24 shows a top view of the duckbill valve member of FIG. 23.
Figure 23:
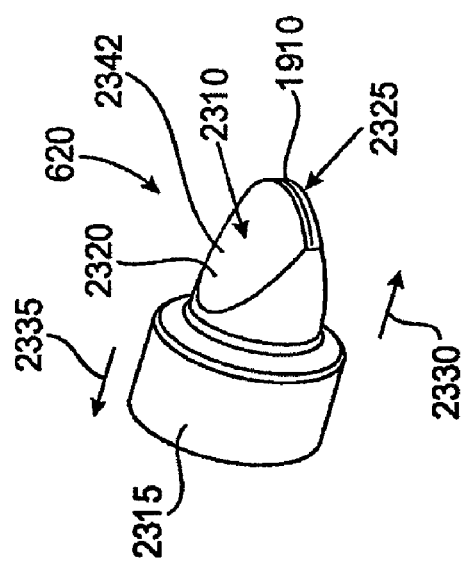
FIG. 23 shows a perspective view of a duckbill valve member of the bronchial isolation device.

Exemplary Valves. In one embodiment, the valve member 620 comprises a duckbill valve that permits flow in one direction and prevents or restricts flow in a second direction. FIGS. 23-25 show an embodiment of a valve member 620 comprised of a duckbill valve 2310 that can be used in the bronchial isolation device 610. The duckbill valve 2310 includes a tubular base 2315 that has an outer diameter that fits within the annular valve protector portion 720 of the frame 615. As best shown in FIGS. 23 and 25, the duckbill valve 2310 includes a pair of opposed, inclined walls 2320 having ends that meet at lips 2325. The lips 2325 meet at two opposed corners. The walls 2320 can move with respect to one another so as to separate at the lips 2325 and form an opening through which fluid can travel. When exposed to fluid flow in a first direction (represented by the arrow 2330 in FIG. 23) at the cracking pressure, the walls 2320 separate from one another to form the opening. When exposed to fluid flow in a second direction (represented by the arrow 2335 in FIG. 23), the walls 2320 remain closed and prevent fluid from flowing through the duckbill valve 2320.

The valve protector portion 720 of the frame 615 provides structural support to the valve member 620 and serves to prevent the valve member 620 from being deformed to the extent that the performance of the valve member 620 is adversely affected. For example, a bronchial passageway can constrict or otherwise change shape during inhalation, exhalation, or cough. The valve protector portion 720 substantially shields the valve member 620 from excessive deformation when the bronchial passageway changes shape. The valve member 620 can optionally include a reinforcement member 2202 comprised of a curved or looped wire that extends between the two corners of the lips and around the duckbill valve 2310 or other type of valve. For clarity of illustration, the reinforcement member is only shown in FIG. 24. The curved wire is rigid so as to provide structural protection to the valve 2310, such as to maintain the distance between the corners of the lips, in the event that the valve 2310 is exposed to forces that might deform the valve 2310. The reinforcement member 2202 may be used in combination with the valve protector portion 720 of the frame, of may be used as a substitute for the valve protector portion 720.

Figure 27:
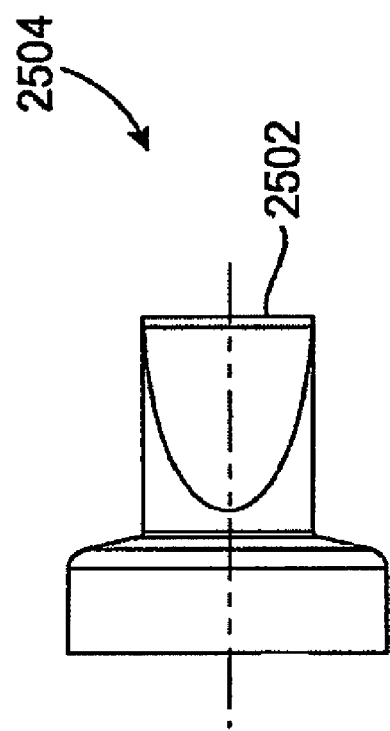
FIG. 27 shows a top view of the duckbill valve member of FIG. 26.
Figure 26:
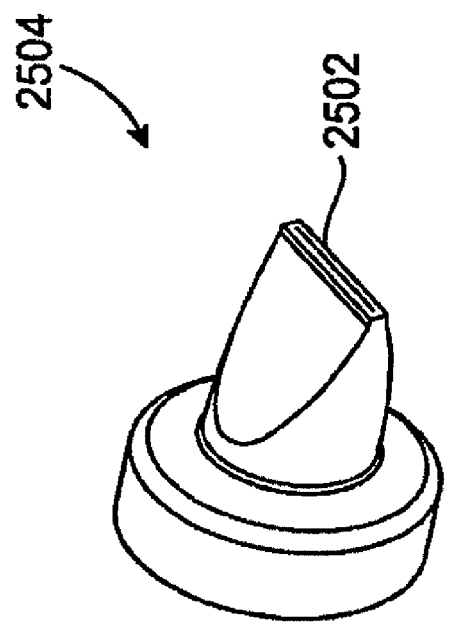
FIG. 26 shows a perspective view of another embodiment of a duckbill valve member with a straight leading edge.

With reference to FIGS. 23-25, the walls 2320 have an outwardly-domed outer surface 2342 and as a leading edge 1910 that forms an outward curve. The curved-shape of the leading edge 1910 provides a longer lips 2325 than the lip for a straight leading edge, such as the straight leading edge 2502 of the duckbill valve 2504 shown in FIGS. 26 and 27. The result is that for a given valve size, the flow rate at a given differential pressure across the lips is higher for a curved leading edge valve than for a straight leading edge valve. Table 1 lists the pressure drop across two duckbill valves, including a duckbill valve with a curved leading edge (i.e., a curved mouth) and a diameter of about 0.128 inches and a duckbill valve with a straight leading edge (i.e., a straight mouth) and a diameter of about 0.116 inches. As shown in Table 1, even though the curved-mouth valve has a smaller diameter, the pressure drop across the curved-mouth valve is lower than the straight mouth valve at both 50 ml/min and 500 ml/min.

TABLE 1

Curved vs. Straight Duckbill Valve Pressure Drop

| Valve Type | Valve Diameter, inches | Pressure Drop Across Valve, in-H$_2$O | |
|---|---|---|---|
| | | 50 ml/min | 500 ml/min |
| Straight Mouth | 0.128 | 0.5 | 2.8 |
| Curved Mouth | 0.116 | 0.4 | 2.4 |

Thus, the curved-mouth duckbill valve provides a higher flow rate than the straight-mouthed duckbill valve, which makes the curved mouth duckbill valve particularly well suited for use in a one-way valve bronchial isolation device. As mentioned above, for bronchial implantation, the higher the flow rate once the valve is cracked open, the better the performance of the valve.

It has been determined that the cracking pressure of a duckbill valve can be altered by changing the angle between the faces of the two lips of the valves. The cracking pressure will be reduced if this angle is reduced, and the cracking pressure will be increased if this angle is increased. As the angle is reduced, the length of the valve increases, and this should be taken into account if a very short valve is desired.

Figure 28A:
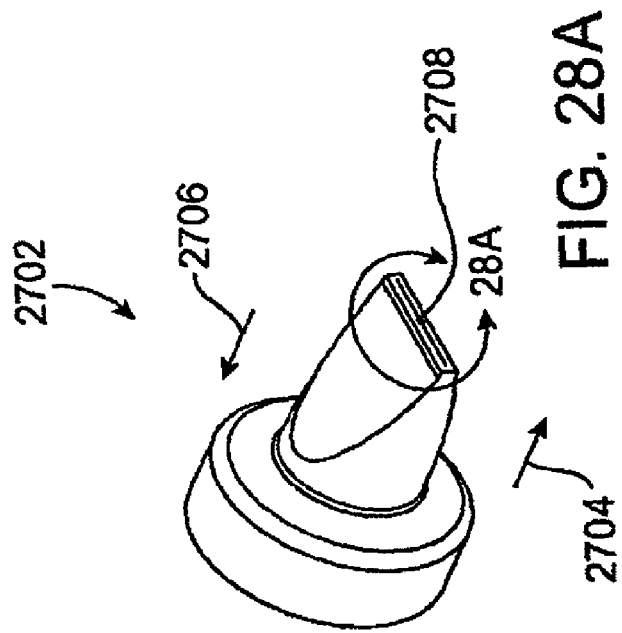
FIG. 28A shows a perspective view of an embodiment of a one-way duckbill valve that provides a controlled flow in a reverse direction.
Figure 28B:
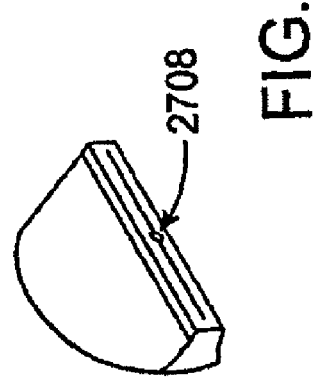
FIG. 28B shows an enlarged, perspective view of a mouth region of the valve of FIG. 28A.

There may be situations where a controlled reverse flow through a one-way valve might be desirable. FIGS. 28A and 28B shows an embodiment of a one-way duckbill valve 2702 that provides a controlled flow in a reverse direction. The valve 2702 behaves as a one-way valve in the forward direction (represented by the arrow 2704 in FIG. 28A) in that the valve 2702 allows free flow of fluid through the valve at or above the valve's cracking pressure. The valve 2704 also allows a small, controlled rate of flow in the reverse direction (represented by the arrow 2706 in FIG. 28A). In this regard, the duckbill valve 2704 includes a small flow channel 2708 that extends through the lips of the valve, as best shown in the enlarged view of FIG. 28B. The flow channel 2708 allows fluid to flow in the reverse direction through the lips. The rate of flow is a function of the diameter and length of the flow channel 2530.

It should be appreciated that the valve member 620 can comprise valve types other than a duckbill valve. For example, the one-way duckbill valve could be replaced with another type of one-way valve, such as a flap valve, a Heimlich valve, a tri-lobe duckbill valve or other multi-lobe valves, a diaphragm valve, a ball valve, etc. In addition, the one-way valve can be replaced with a blocking element to prevent flow through the device in either direction, or a two-way valve to allow controlled flow in both directions, or one-way or two-way valves that are designed to allow the passage of a catheter to suction, inject therapeutic substances or otherwise treat the isolated lung region distal to the implanted bronchial isolation device.

Use and Deployment of the Bronchial Isolation Device.

Figure 29:
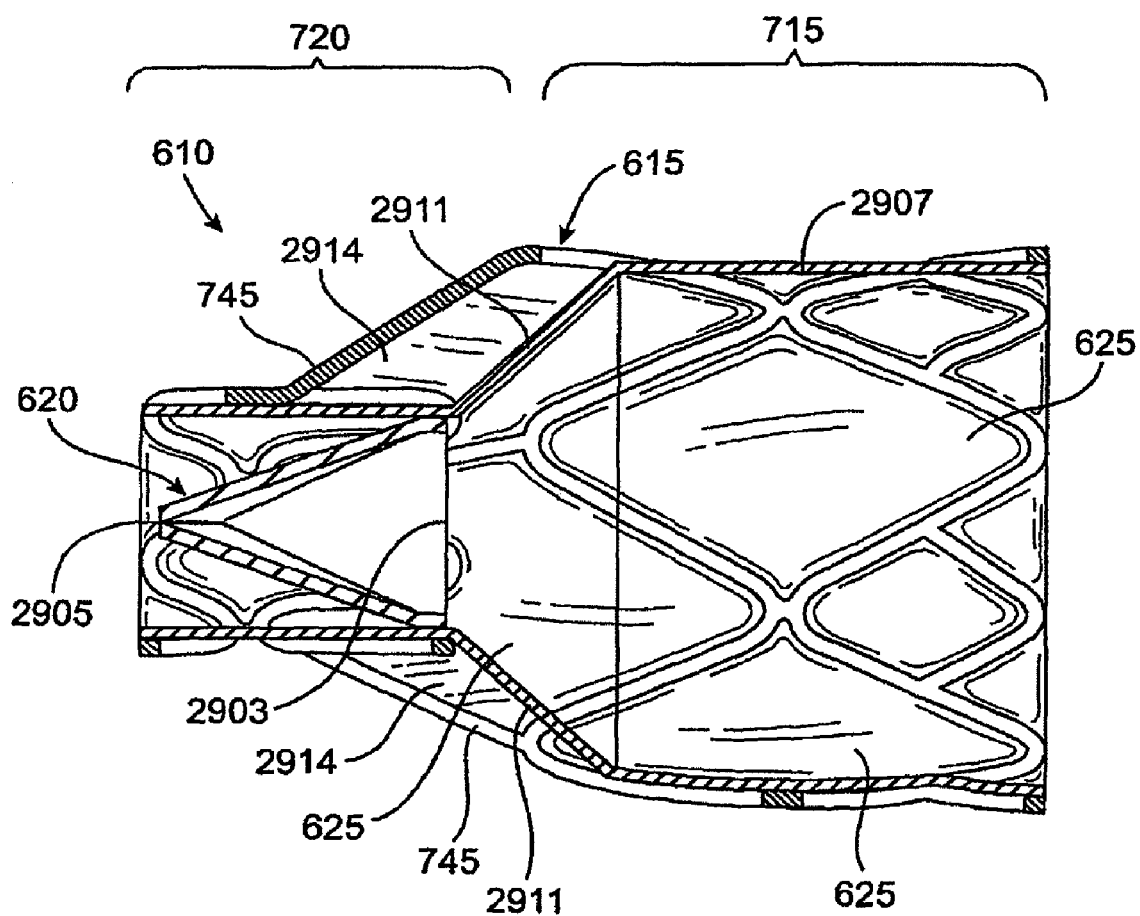
FIG. 29 shows a cross-sectional view of the bronchial isolation device employing the frame of FIGS. 15 and 16.

FIG. 29 shows a cross-sectional view of the flow control device 610 employing the embodiment of the frame 615 shown in FIGS. 15 and 16. The valve member 620 is mounted within the valve protector portion 720 of the frame 615. The membrane 625 is attached to the valve member 620 at one or more locations to secure the valve member 620 to the frame 615. The valve member is positioned such that an entry mouth 2903 is located at a distal region of the valve protector portion 720 and an exit mouth 2905 is located at a proximal region. The valve protector portion 720 at least partially surrounds the valve member 620 to maintain a default shape of the valve member 620. For example, if the bronchial passageway deforms while the bronchial isolation device 610 is mounted therein, the valve protector portion 720 protects the valve member 620 from deformation. The default shape of the valve member 620 can be a closed configuration that prohibits fluid flow or the default shape can be some other default shape.

The membrane 625 is positioned in a web-like manner within the cells 712. The membrane 625 covers or is connected to at least a portion of the frame 615. The membrane covers at least a portion of the retainer portion 715 and can also cover at least a portion of the valve protector portion 720. The membrane 625 can cover the entire retainer portion 715 or it can cover a portion of the retainer portion 715. In addition, the membrane 625 can cover the entire valve protector portion 720 or it can cover a portion of the valve protector portion 720.

The membrane 625 defines a fluid pathway that is open at a distal end of the frame 615 and that leads into the entry mouth 2903 of the valve 620. The general outer contour of the fluid pathway is represented by a bold line 2907 in FIG. 29. In the valve protector portion 715, the membrane 625 follows the outer contour of the frame 615 such that the fluid pathway is generally cylindrical in this portion of the frame 615. However, it is not necessary that the fluid pathway be cylindrical as long as it leads into the entry mouth 2903 of the valve member 620. Moreover, it is not necessary that the membrane cover the entire bronchial isolation device 610 as long as the membrane forms the fluid pathway. Moving toward the valve member 625, the outer contour of the membrane 625 slopes radially inward (as exhibited by the bold lines 2911) moving toward the entry mouth 2903 of the valve member 620. In this manner, the membrane 625 forms a funnel-shaped fluid pathway that leads into the valve member 620. The membrane 625 also forms radially-extending fins 2914 between the outer membrane wall of the funnel-shaped fluid pathway and the linking struts 745.

Figure 30:
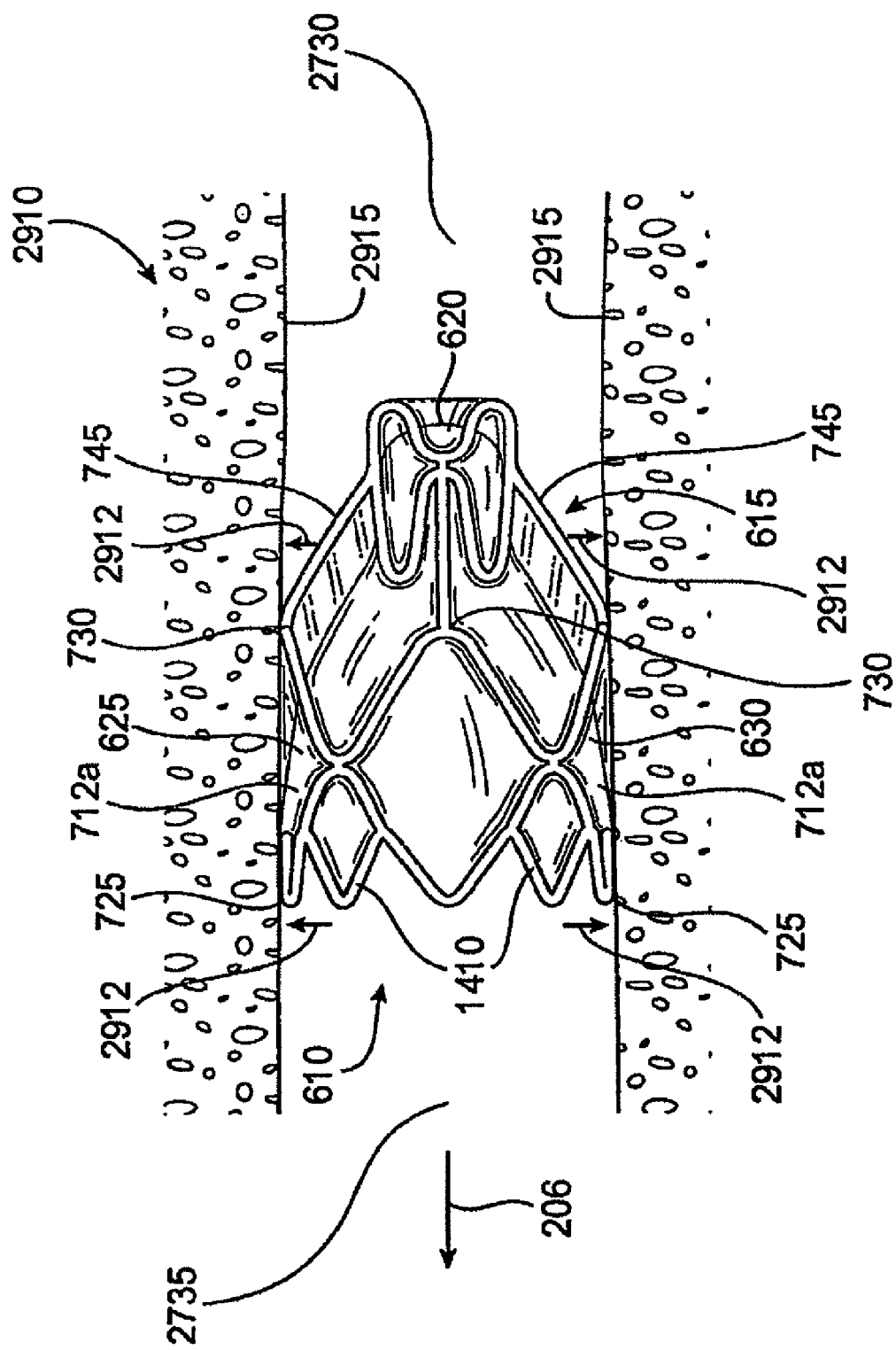
FIG. 30 shows a bronchial isolation device deployed in a bronchial passageway.

FIG. 30 shows a cross-sectional view of bronchial passageway 2910 having interior walls 2915 that define a lumen of the bronchial passageway 2910. As is known to those skilled in the art, fluids can travel to and from a region of the lung through the lumen of the bronchial passageway 2910. The embodiment of the bronchial isolation device 610 of FIG. 29 is shown positioned within the bronchial passageway 2915. The bronchial isolation device 610 is shown in FIG. 30 with the membrane 625 trimmed along the distal edge of the frame 615. When the bronchial isolation device 610 is positioned within the bronchial passageway 2910, the frame 615 is in an expanded state so that it exerts a radial force against the interior walls 2915, as represented by the arrows 2912 in FIG. 29. The radial force causes the frame 615 to press against the bronchial wall 2915 with a pressure sufficient to retain the bronchial isolation device 610 in a fixed position relative to the bronchial passageway. The distal edges 725 of the retainer cells 712*a* are positioned such that they lodge against the interior walls 2915 and inhibit the bronchial isolation device 610 from migrating in the distal direction 206.

As discussed above, the proximal edges 730 of the retainer cells 712a are attached to the linking struts 745. The linking struts 745 provide a smooth transition between the retainer section and the valve protector section of the frame 615. The linking struts 745 also lessen any sharpness of the proximal edges 730 of the retainer cells 712a and prevent the proximal edges 730 from penetrating into the bronchial wall 2915 if the bronchial isolation device 610 is pulled in the proximal direction 204 during removal. In addition, the linking struts 745 assist in radially constricting the retainer section of the frame 615 during removal of the bronchial isolation device 610. When the valve protector section is radially constricted (such as by using forceps that are deployed to the location of the bronchial isolation device 610), the linking struts 745 transfer the radial constriction to the retainer section of the frame 615.

Figure 31:
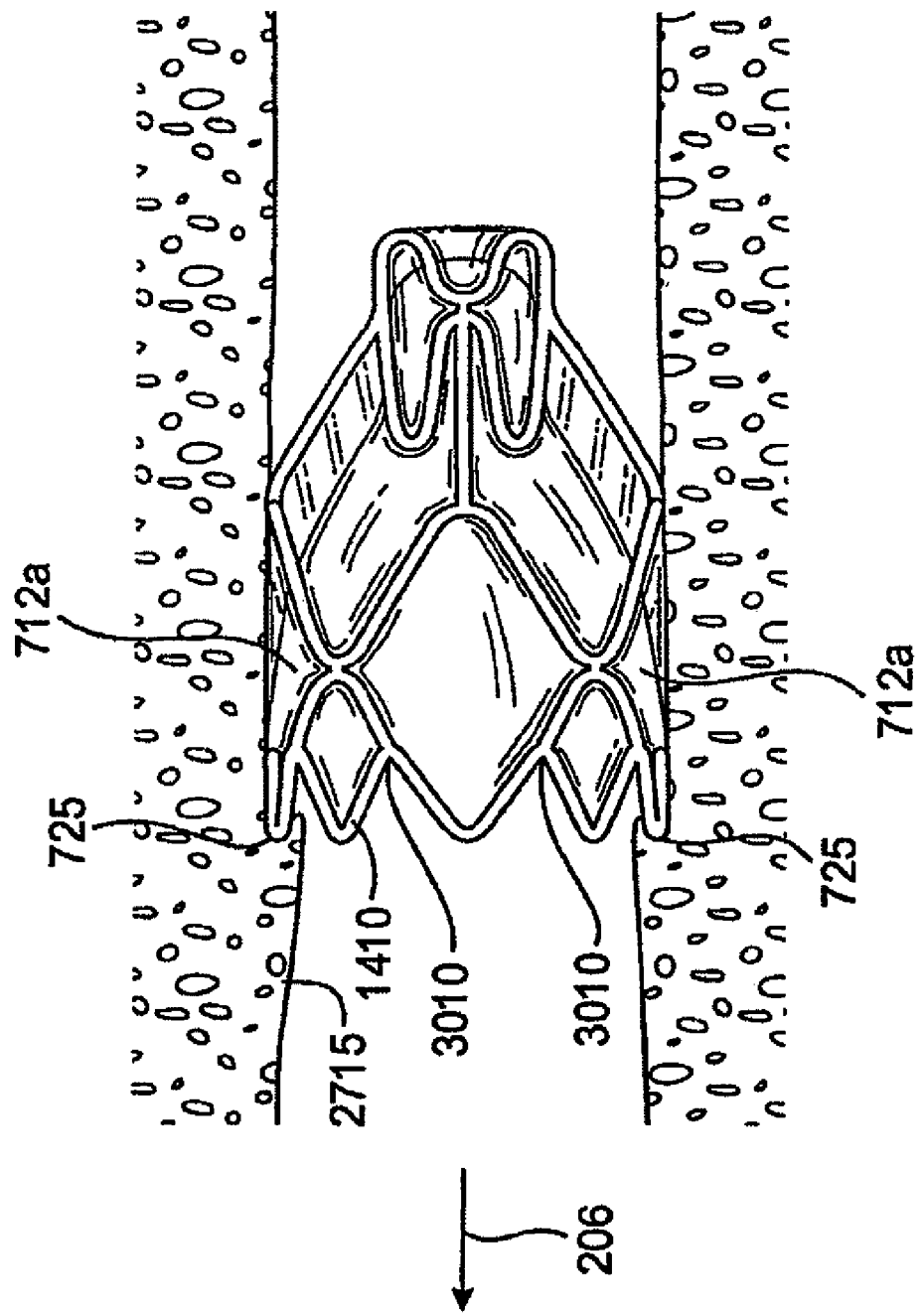
FIG. 31 shows a bronchial isolation device deployed in a bronchial passageway and partially embedded in a bronchial wall of the passageway.

As discussed above, the frame 615 can optionally include one or more distal cross struts 1410 and one or more proximal cross struts 1415. The cross struts 1410, 1415 function to limit the distance that the cells 712 can penetrate into the bronchial wall 2915. For example, FIG. 31 shows the bronchial isolation device 610 after it has migrated in the distal direction 206 such that some of the distal edges 725 of the retainer cells 712a have penetrated into the bronchial wall 2915. The connection point 3010 between the distal cross strut 1410 and the cell 712a provides a stopping point that will prevent the retainer cell 712a from penetrating any deeper beyond the connection point 3010.

Figure 32A:
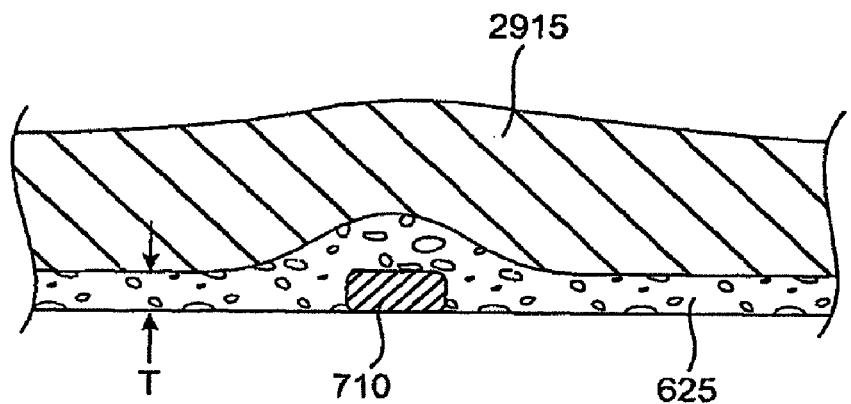
FIG. 32A-32C each show an enlarged view of the portion of the flow control device that forms a seal with the bronchial wall.

With reference again to FIG. 30, the expanded frame 615 presses against the bronchial wall 2915 so that the bronchial isolation device 610 20 sealingly engages the bronchial wall 2915 around the entire circumference of the bronchial isolation device 610. The seal can be formed between the frame 615 and the bronchial wall 2915, between the membrane 625 and the bronchial wall 2915, between both the membrane 625/frame 615 and the bronchial wall 2915, or any combination thereof. For example, FIG. 32A shows an enlarged view of the portion of the flow control device 610 that forms a seal with the bronchial wall 2915. In the embodiment of FIG. 32A, the membrane 625 is positioned between a frame strut 710 and the bronchial wall 2915 such that the membrane 625 seals with the bronchial wall 2915. The situation shown in FIG. 32A corresponds to use of the frame/membrane configuration shown in FIGS. 17A, 17B.

Figure 32B:
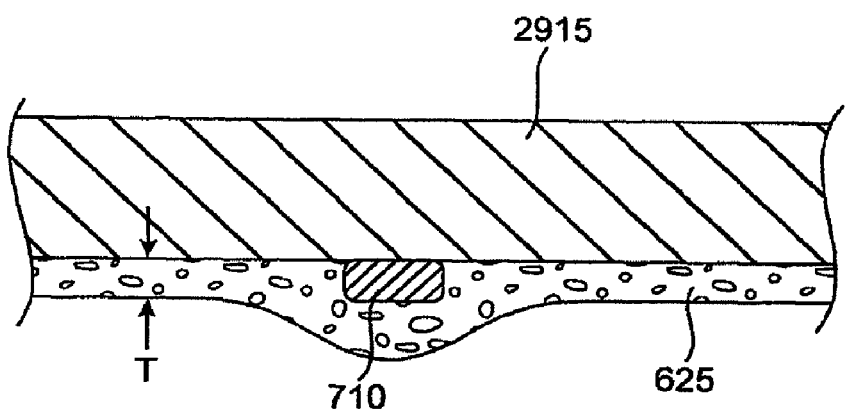

In another embodiment, shown in FIG. 32B, both the membrane 625 and the frame strut 710 seal with the bronchial wall 2915. The situation shown in FIG. 32B corresponds to use of the frame/membrane configuration shown in FIG. 17C.

Figure 32C:
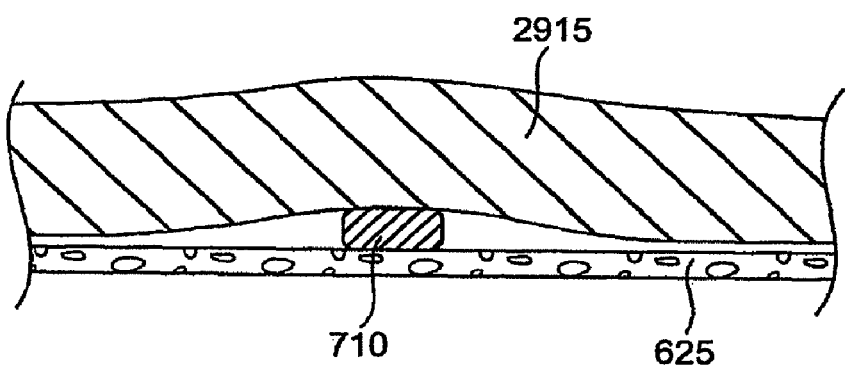

In another embodiment, shown in FIG. 32C, the frame strut 710 seals with the bronchial wall 2915 but the membrane 710 does not necessarily seal with or contact the bronchial wall 2915. The situation shown in FIG. 32C corresponds to use of the frame/membrane configuration shown in FIG. 17D.

In the embodiment shown in FIG. 30, the frame 615 is sealed with the bronchial wall 2915. It should be appreciated that the seal can occur at any location along the frame 615 as long as the membrane 625 provides a fluid pathway between the location of the seal and the valve member 620. As mentioned, the cross struts 1410 create additional cells that permit the frame to flex at different locations along its length. In this manner, the struts that form the cells can form independent and redundant seals with the bronchial wall 2915.

Thus, the frame 615 and/or the membrane 625 provide a seal that prevents fluid from flowing between the interior walls 2915 and the bronchial isolation device 610. The membrane 625 engages with the portion of the bronchial isolation device that is sealed to the bronchial wall 2915 such that the fluid pathway formed by the membrane directs fluid into the valve member 620 so that fluid must flow through the valve member 620 in order to flow from a proximal side 2730 of the bronchial isolation device 610 to a distal side 2735 or vice-versa. That is, the sealing engagement between the bronchial isolation device 610 and the bronchial wall 2915 prevents fluid from flowing around the periphery of the bronchial isolation device 610, thereby forcing fluid flow to occur through the membrane path and into the valve member 620. In this manner, the membrane 625 provides a fluid pathway into the valve member 620. It is not necessary for the membrane 625 to cover the entire bronchial isolation device as long as the membrane 625 forms a pathway from the location of the seal to the entry mouth of the valve member 620.

It should be appreciated that in certain circumstances it may be desirable to permit a limited amount of fluid to flow around the bronchial isolation device rather than through the valve member. In such circumstances, the bronchial isolation device 610 can be modified to permit such limited flow.

The bronchial isolation device 610 can be deployed to a desired location in a bronchial passageway according to a variety of methods. In one embodiment, the bronchial isolation device is coupled to the distal end of a delivery catheter, which is then inserted through the patient's mouth or nose, into the trachea, and to the location in the bronchial passageway. The bronchial isolation device 610 is then uncoupled from the delivery catheter such that it is positioned at a desired location in the bronchial passageway.

Figure 33:
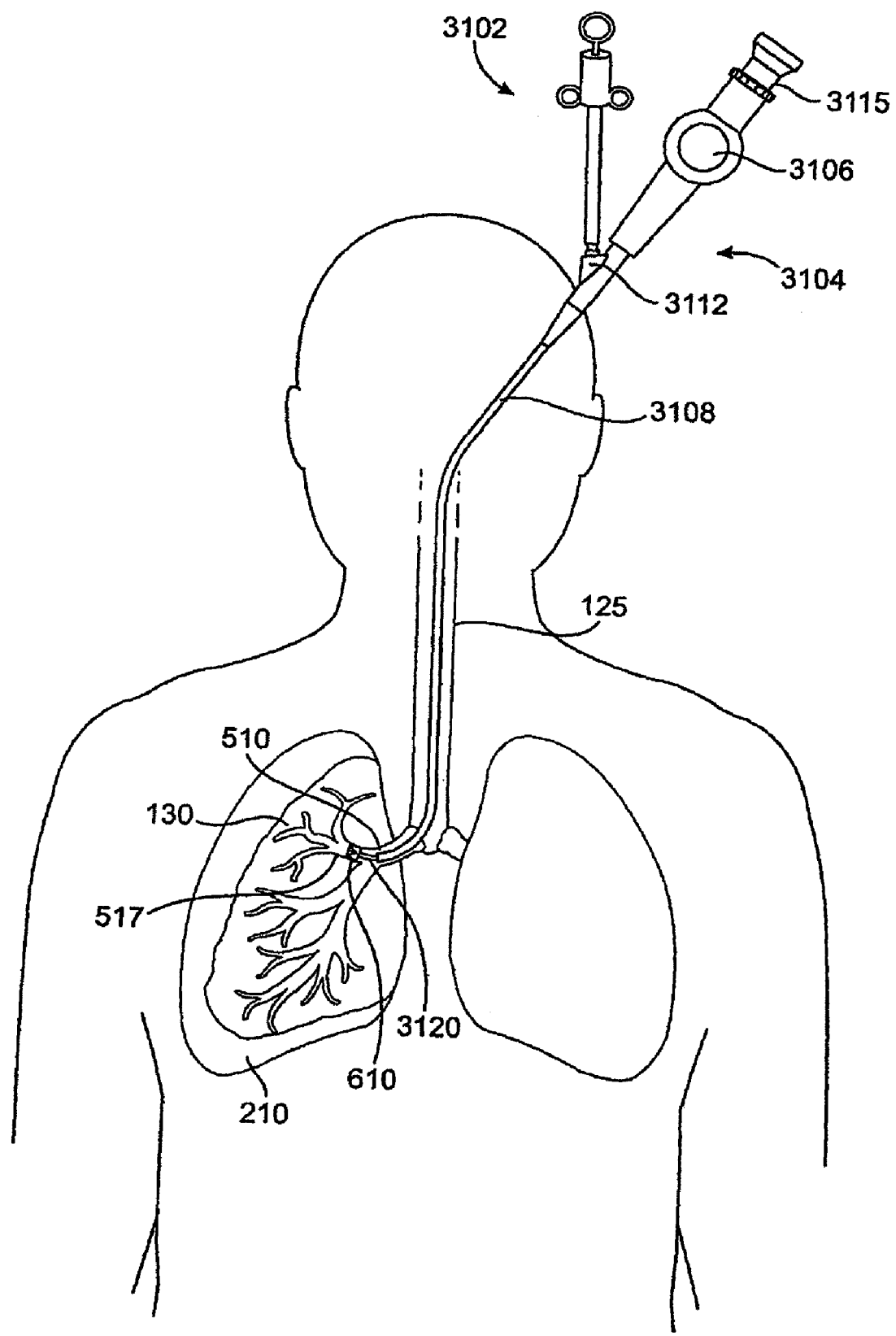
FIG. 33 shows a bronchoscope deployed within a bronchial tree of a patient for delivering a bronchial isolation device into a bronchial passageway.

With reference to FIG. 33, a delivery catheter 3102 can be deployed using a bronchoscope 3104, which in an exemplary embodiment has a steering mechanism 3106, a shaft 3108, a working channel entry port 3112, and a visualization eyepiece 3115. The bronchoscope 3104 has been passed into a patient's trachea 125 and guided into the right primary bronchus 510 according to well-known methods. The delivery catheter 3102 is then inserted into the bronchoscope through the working channel entry port 3112 and fed into the working channel so the distal end 3120 of the delivery catheter (and the attached bronchial isolation device 610) protrude out of the distal end of the bronchoscope. The bronchial isolation device 610 is then released from the delivery catheter so that the frame 615 expands and anchors at a desired location, as shown in FIG. 1.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A method for modifying air flow in a bronchial passageway of a lung, the method comprising:
advancing a delivery catheter through a bronchoscope so that a distal end of the delivery catheter and an attached flow control device protrude out of a distal end of the bronchoscope and into the bronchial passageway;
releasing the flow control device from the delivery catheter to allow a retainer region of the flow control device, which is at least partially covered with a membrane, to move from a contracted state to an expanded state to form a seal with an interior wall of the bronchial passageway to retain the flow control device in a fixed location therein; and removing the delivery catheter from the bronchial passageway, leaving the flow control device in the passageway to modify air flow therethrough,
  wherein a valve member disposed in the flow control device permits air flow in an exhalation direction and limits air flow in an inhalation direction,
  wherein the membrane provides a fluid pathway from the seal to the valve member to direct air flowing through the bronchial passageway into the valve member,
  wherein the valve member is disposed in a valve protector region of the flow control device, which is connected to the retainer region, and wherein, upon release, the retainer region expands to a larger diameter than an expanded diameter of the valve protector region.

2. A method as in claim 1, wherein releasing the flow control device in the bronchial passageway comprises releasing the device in a lobar bronchus, which feeds into a lobe of the lung.

3. A method as in claim 1, wherein releasing the flow control device in the bronchial passageway comprises releasing the device in a segmental bronchus, which feeds into a bronchopulmonary segment of the lung.

4. A method as in claim 1, further comprising repeating the steps with at least a second flow control device in at least one a second bronchial passageway of the lung.

5. A method as in claim 4, wherein the flow control devices are released in at least two segmental bronchi providing air flow to at least two bronchopulmonary segments of one lobe of the lung.

6. A method as in claim 1, wherein the valve member partially limits air flow in an inhalation direction and permits air flow in the exhalation direction.

7. A method as in claim 1, wherein the valve member blocks air flow in an inhalation direction and permits air flow in the exhalation direction.

8. A method as in claim 1, wherein the retainer region and the valve protector region comprise a frame, and wherein the membrane covers the entire frame to form a continuous pathway for air through the flow control device.

9. A method for modifying air flow in a segmental bronchus, which feeds into a bronchopulmonary segment of a lung, the method comprising:

advancing a delivery catheter through a bronchoscope so that a distal end of the delivery catheter and an attached flow control device protrude out of a distal end of the bronchoscope and into the segmental bronchus;

releasing the flow control device from the delivery catheter to allow a retainer region of the flow control device, which is at least partially covered with a membrane, to move from a contracted state to an expanded state to form a seal with an interior wall of the segmental bronchus to retain the flow control device in a fixed location therein; and removing the delivery catheter from the segmental bronchus, leaving the flow control device in the segmental bronchus to modify air flow therethrough,
  wherein a valve member disposed in the flow control device permits air flow in an exhalation direction and limits air flow in an inhalation direction,
  wherein the membrane provides a fluid pathway from the seal to the valve member to direct air flowing through the segmental bronchus into the valve member,
  wherein the valve member is disposed in a valve protector region of the flow control device, which is connected to the retainer region, and wherein, upon release, the retainer region expands to a larger diameter than an expanded diameter of the valve protector region.

10. A method as in claim 9, further comprising repeating the steps with at least a second flow control device in at least a second segmental bronchus that feeds a second bronchopulmonary segment of the lung, wherein the two bronchopulmonary segments are located in one lobe of the lung.

11. A method as in claim 9, further comprising repeating the steps with at least a second flow control device in at least a second segmental bronchus that feeds a second bronchopulmonary segment of the lung, wherein the two bronchopulmonary segments are located in two different lobes of the lung.

12. A method as in claim 9, wherein releasing the flow control device in the segmental bronchus causes the bronchopulmonary segment to collapse.

* * * * *